United States Patent
Marsh

(10) Patent No.: US 10,864,328 B2
(45) Date of Patent: Dec. 15, 2020

(54) DRIVE MECHANISM FOR A DRUG DELIVERY DEVICE

(71) Applicant: Sanofi, Paris (FR)

(72) Inventor: William Marsh, Buckingham (GB)

(73) Assignee: Sanofi, Paris (FR)

(*) Notice: Subject to any disclaimer, the term of this patent is extended or adjusted under 35 U.S.C. 154(b) by 680 days.

(21) Appl. No.: 14/915,821

(22) PCT Filed: Sep. 3, 2014

(86) PCT No.: PCT/EP2014/068644
§ 371 (c)(1),
(2) Date: Mar. 1, 2016

(87) PCT Pub. No.: WO2015/032771
PCT Pub. Date: Mar. 12, 2015

(65) Prior Publication Data
US 2016/0213855 A1    Jul. 28, 2016

(30) Foreign Application Priority Data

Sep. 3, 2013 (EP) .................................. 13182747

(51) Int. Cl.
*A61M 5/315* (2006.01)
*A61M 5/20* (2006.01)

(52) U.S. Cl.
CPC .......... *A61M 5/31566* (2013.01); *A61M 5/20* (2013.01); *A61M 5/31553* (2013.01);
(Continued)

(58) Field of Classification Search
CPC ................ A61M 5/31566; A61M 5/20; A61M 5/31553; A61M 5/31583; A61M 5/31535;
(Continued)

(56) References Cited

U.S. PATENT DOCUMENTS

2002/0120235 A1* 8/2002 Enggaard ............... A61M 5/20
604/135
2008/0108953 A1    5/2008 Moser et al.
2012/0253274 A1   10/2012 Karlsson et al.

FOREIGN PATENT DOCUMENTS

| JP | 2008-043761 | 2/2008 |
| JP | 2009-502273 | 1/2009 |
| JP | 2012-522547 | 9/2012 |
| WO | WO02/053214 | 7/2002 |
| WO | WO2006/039930 | 4/2006 |
| WO | WO2007/017052 | 2/2007 |

(Continued)

OTHER PUBLICATIONS

International Search Report and Written Opinion in International Application No. PCT/EP2014/068644, dated Feb. 12, 2015, 11 pages.

(Continued)

*Primary Examiner* — Bhisma Mehta
*Assistant Examiner* — Hong-Van N Trinh
(74) *Attorney, Agent, or Firm* — Fish & Richardson P.C.

(57) ABSTRACT

A drive mechanism (4) for a drug delivery device comprising—a piston rod (14), —a trigger member (9) coupled with the piston rod (14) in such a manner that rotational movement between the piston rod (14) and the trigger member (9) is constrained in a first state, the trigger member (9) being elastically deformable in such a manner that the piston rod (14) is rotationally moveable with respect to the trigger member (9) in a second state, —a trigger button (10) being suitable for activating the deformation of the trigger member (9).

19 Claims, 19 Drawing Sheets

(52) U.S. Cl.
CPC ..... *A61M 5/31583* (2013.01); *A61M 5/31535* (2013.01); *A61M 2205/581* (2013.01); *A61M 2205/582* (2013.01); *A61M 2205/583* (2013.01)

(58) Field of Classification Search
CPC .......... A61M 5/31533; A61M 5/31541; A61M 5/31545; A61M 5/31548; A61M 5/3155; A61M 5/31565; A61M 2005/2006; A61M 2005/202; A61M 2005/2026; A61M 5/24; A61M 5/315; A61M 5/31501; A61M 5/3159; A61M 5/31593; A61M 5/31536; A61M 5/3158; A61M 5/31551; A61M 2205/581; A61M 5/31585; A61M 2005/2407; A61M 5/31543
See application file for complete search history.

(56) References Cited

FOREIGN PATENT DOCUMENTS

| WO | WO2010/115670 | 10/2010 |
| WO | WO2011/043605 | 4/2011 |
| WO | WO2011/053225 | 5/2011 |
| WO | WO2012/063061 | 5/2012 |

OTHER PUBLICATIONS

International Preliminary Report on Patentability in International Application No. PCT/EP2014/068644, dated Mar. 8, 2016, 8 pages.
Rote Liste, "50. Hypophysen-, Hypothalamushormone, andere regulatorische Peptide u. ihre Hemmstoffe," Chapter 50, ed. 2008, 20 pages.

* cited by examiner

DRIVE MECHANISM FOR A DRUG DELIVERY DEVICE

CROSS-REFERENCE TO RELATED APPLICATIONS

This application is a U.S. national stage application under 35 USC § 371 of International Application No. PCT/EP2014/068644, filed on Sep. 3, 2014, which claims priority to European Patent Application No. 13182747.9, filed on Sep. 3, 2013, the entire contents of which are incorporated herein by reference.

The invention concerns a drive mechanism for a drug delivery device.

In a drug delivery device, a piston within a cartridge that contains a drug may be displaced by a piston rod, thereby delivering a dose. The drug delivery device comprises a drive mechanism which allows setting and delivering the dose by means of piston rod movement. During the dose setting phase, the piston rod is not moved distally; in the dose delivery phase, it is.

WO 2011/043605 shows a drug delivery device comprising a piston rod running through a nut in such a manner that rotational movement between the components is constrained, wherein the nut is held by an elastically deformable stopper piece that has been deformed during assembly of the device, thereby constraining rotational movement of the nut.

WO 2011/053225 shows a drug delivery device comprising a deformable ring-shaped locking member which constrains relative movement between two housing parts.

It is an aim of the invention to provide a drive mechanism which prevents movement before the delivery phase and permits it during the delivery phase.

This aim is achieved by a drive mechanism for a drug delivery device comprising
  a piston rod,
  a trigger member coupled to the piston rod in such a manner that rotational movement between the piston rod and the trigger member is constrained in a first state, the trigger member being elastically deformable in such a manner that the piston rod is rotationally moveable with respect to the trigger member in a second state,
  a trigger button being suitable for activating the deformation of the trigger member.

The trigger member can be moved out of constraining engagement by elastic deformation, thereby enabling rotational movement of the piston rod. The piston rod and the trigger member can be coupled directly or indirectly by means of a further component e.g. a nut.

One embodiment of the drive mechanism further comprises a trigger nut that is axially movable with respect to the piston rod, the trigger nut being coupled to the piston rod in such a manner that rotational movement between the trigger nut and the piston rod is constrained. The trigger member engages with the trigger nut in such a manner that rotational movement between the trigger nut and the trigger member is constrained in the first state, the trigger member being elastically deformable in such a manner that the trigger member disengages from the trigger nut in the second state, thereby allowing for rotational movement of the trigger nut with respect to the trigger member.

Elastically deforming the trigger member for allowing for rotation of the piston rod and then returning of the elastically deformable trigger member to its biased state in which the piston rod is constrained to rotate constitutes an easy way of switching between the drug delivery (or second) state and the dose setting (or first) state, which are the states of the device during normal operation. Moreover, the elasticity ensures that the drive mechanism returns to a defined state when the trigger button is no longer being pushed.

A drug delivery device is suitable for delivery of one or more doses of drugs contained in a cartridge. The doses may be fixed or variable. The drug delivery device may be of the injector type suitable for injecting. The drug delivery device is reusable or disposable. In one embodiment, the drug delivery device is a pen-type drug delivery device.

A drive mechanism is a part of the drug delivery device that allows setting a dose and delivering the drug, e.g. by ejecting the drug out of the cartridge.

The term "piston rod" shall preferably mean a component adapted to operate through/within a housing of the drug delivery device, which may be designed to transfer axial movement through/within the medication delivery device preferably to the piston, for example for the purpose of discharging/dispensing an injectable product. Said piston rod may be flexible or not. It may be a simple rod, a lead-screw, a rack-and-pinion system, a worm gear system, or the like. "Piston rod" shall further mean a component having a circular or non-circular cross-section. It may be made of any suitable material known by a person skilled in the art and may be of unitary or multipart construction.

A button may be a simple switch mechanism for controlling some aspect of the drug delivery device. The surface of the trigger button may be flat or shaped to accommodate a human finger tip so as to be easily pressed or pushed.

A nut may be a fastening means or holding means usually having a hole. Further means for fastening or holding a component running through the nut may be provided in the hole, e.g. splines.

"Elastic"/"elastically" corresponds to a property of an element which returns to its original shape after the stress that caused its deformation is no longer applied. Elasticity may be a physical property of a material that forms such element.

Constraining a motion means preventing or avoiding this specific motion. Nevertheless, slight movement due to play or slackness of the components may still be possible.

A movement of the trigger button towards the trigger nut may cause the elastic deformation of the trigger member, which provides the user with an easy way of triggering.

In one embodiment, the trigger button and the trigger member are made in one piece, which forms a robust trigger.

The trigger member may comprise a trigger engagement means engaging with a nut engagement means of the trigger nut, the trigger engagement means being moved away from the nut engagement means when the trigger member is deformed. In other words, switching from engagement to release is achieved by pushing the trigger button, thereby deforming the trigger member; switching from release to engagement is achieved by stopping pushing the trigger button.

The trigger engagement means is located offset to the connection between the trigger button and the trigger member. Since a deforming force is applied in the direction running along the connection between the trigger button and the trigger member, placing the trigger engagement means beyond the direction of the user-applied deforming force means placing the trigger engagement means on a part of the trigger member which moves away from the direction and the trigger nut during deformation.

One embodiment of the trigger nut comprises a multitude of circumferentially arranged teeth that are extending radially from the axis of the piston rod, wherein the trigger engagement means comprises a protrusion that is suitable for engaging with a gap between two teeth of the trigger nut. Due to the toothed-wheel-shape of the trigger nut, the protrusion may engage with any gap between two teeth on the trigger nut's side face.

One embodiment of the trigger member may comprise a sleeve-like part which allows for holding the trigger nut. The trigger member may comprise at least one fixing means suitable for being connected with a housing of the drug delivery device in order to fix the position of the trigger member with respect to the housing. Moreover, the housing via the fixing means reacts the force applied to the trigger button.

The trigger member may be splined with the piston rod, which is a simple connection technique permitting only axial movement between the components.

The drive mechanism may further comprise a drive sleeve axially movable with respect to the piston rod, the drive sleeve being coupled to the piston rod in such a manner that rotational movement between the drive sleeve and the piston rod is constrained. A spring member, e.g. a twistable helical compression spring, is coupled to the drive sleeve in such a manner that it is compressed when the drive sleeve moves proximally with respect to the piston rod. The drive sleeve drives the piston rod during drug delivery, the drive sleeve being actuated by the spring that has been charged during the dose setting state. This spring-loaded drive mechanism may be similar to the design of an auto-injector, which, however can be used only once in contrast to the multi-dose drug delivery device as described.

The drive mechanism may further comprise a dial sleeve that is threadedly coupled to the drive sleeve, the spring member being connected to the dial sleeve in such a manner that the spring member is compressed in the first state by a helical movement of the dial sleeve with respect to the drive sleeve. The spring member at least partly relaxes when rotational movement of the piston rod is allowed in the second state, thereby rotating the drive sleeve with respect to the dial sleeve, wherein the drive sleeve moves distally. The dial sleeve allows for setting a variable dose.

The piston rod may be embodied as a lead screw, wherein rotational movement is transformed into lateral movement.

Other features will become apparent from the following detailed description when considered in conjunction with the accompanying drawings.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Figure 1:
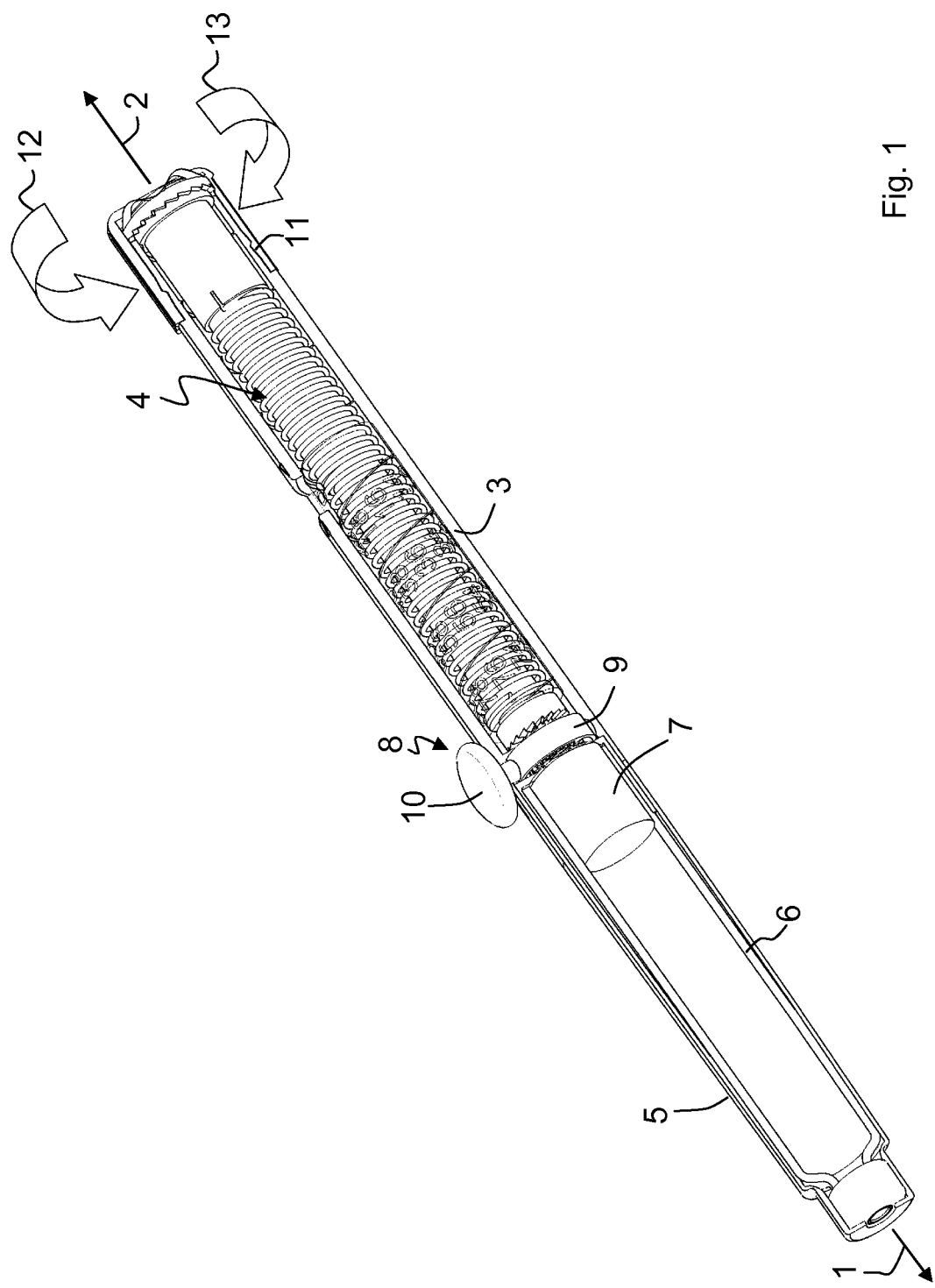
FIG. 1 shows an embodiment of a drive mechanism incorporated into an exemplary drug delivery device.

FIG. 1 illustrates a drive mechanism incorporated into a drug delivery device, which may be a pen injector as an exemplary embodiment, by means of a cut-away view of the drug delivery device. FIG. 1 shows major components, e.g. body 3, cartridge holder 5, trigger 8, dial member 11, cartridge 6 and bung 7.

The drug delivery device has a distal end that is the drug dispensing end and a proximal end on the opposite side. The term "distal end" of the drug delivery device or a component thereof may refer to that end of the device or the component which is closest to the dispensing end of the device. The term "proximal end" of the drug delivery device or a component thereof may refer to that end of the device or the component which is furthest away from the dispensing end of the device. Arrow 1 shows the respective distal direction. Arrow 2 shows the proximal direction.

The drug delivery device comprises a body 3 that forms a proximal part of a housing being suitable for holding and protecting a drive mechanism 4. The body 3 may be an elongated sleeve-shaped part. A cartridge holder 5 forms a distal part of the housing being suitable for holding and protecting a cartridge 6. The cartridge holder 5 may be an elongated sleeve-shaped part having a narrowing distal part. The body 3 and the cartridge holder 5 are connected to each other. The connection may be releasable or not.

The term "housing" shall preferably mean any exterior housing ("main housing", "body", "shell") or interior housing ("insert", "inner body") which may have a unidirectional axial coupling to prevent proximal movement of specific components. The housing may be designed to facilitate the safe, correct and comfortable handling of the medication delivery device or any of its mechanisms. Usually, it is designed to house, fix, protect, guide, and/or engage with any of the inner components of the medication delivery device (e.g. the drive mechanism, cartridge, piston, piston rod, lead screw), preferably by limiting the exposure to contaminants, such as liquid, dust, dirt etc. In general, the housing may be unitary or a multipart component of tubular or non-tubular shape.

The cartridge 6 contains the drug or medicament. It has a distal end covered by a membrane that may be punctured by a needle (not shown) for drug delivery. A bung 7 is located at the proximal end of the cartridge 6, the bung 7 being moveable distally along the inner side wall of the cartridge 6, thereby reducing the volume of the drug containing the chamber of the cartridge 6 so that the drug is ejected through the needle.

The drive mechanism 4 is located in the body 3, the drive mechanism 4 being suitable for moving the bung 7 in the distal direction 1, thereby delivering the drug. The drive mechanism 4 comprises a trigger 8 including a trigger member 9 and a trigger button 10 for initiating the drug delivery as described later.

The drug delivery device further comprises a dial member 11 located at the proximal end of the drug delivery device. The dial member 11 is rotatably moveable with respect to the body 3 in a first direction, which is the clockwise direction 12 in this embodiment, and a second direction, which is the counter-clockwise direction 13 in this embodiment.

The drug delivery device can be operated to deliver a number of user-variable doses of a drug from the cartridge 6 via a needle (not shown). The drug delivery device is disposable and is delivered to the user in a fully assembled condition ready for use.

Figure 2:
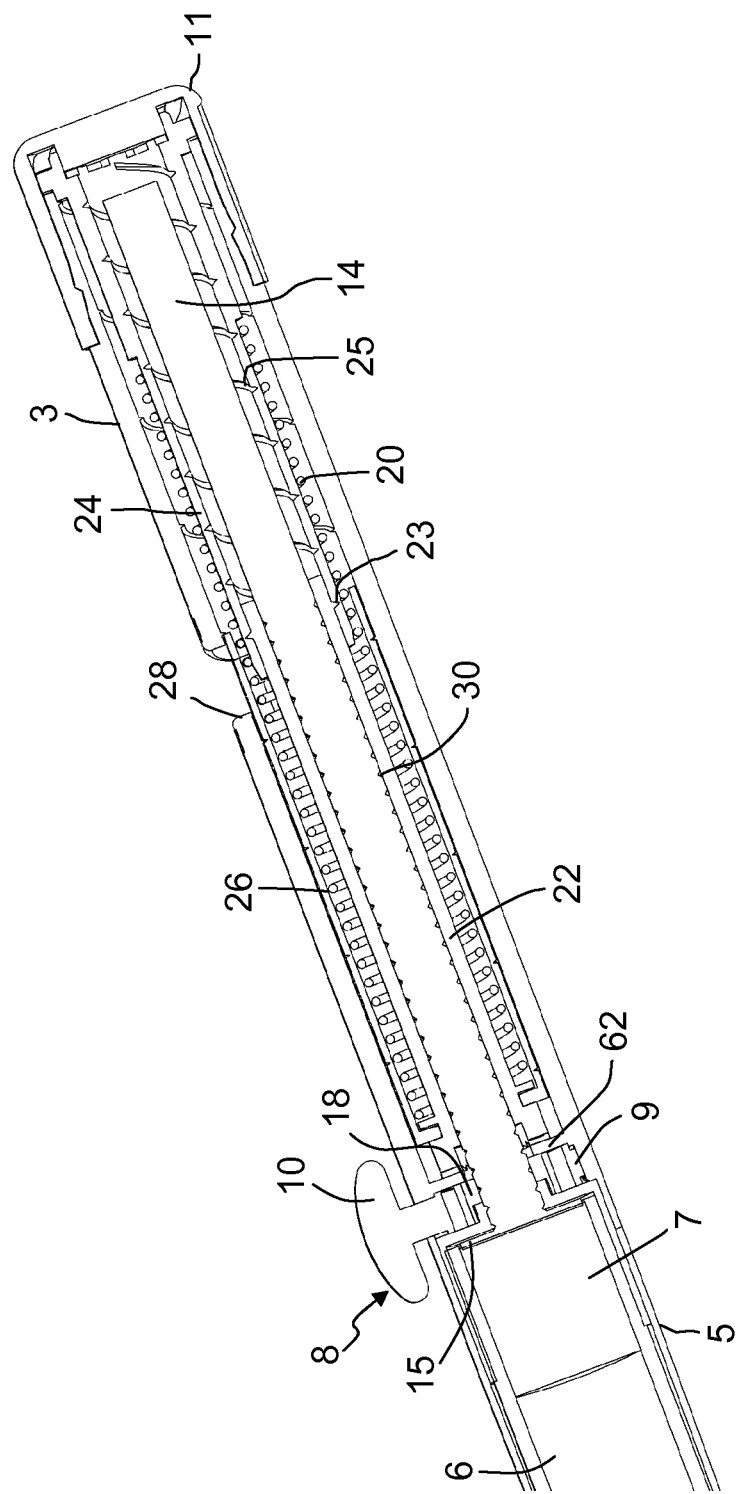
FIG. 2 shows a cross-sectional view of the drive mechanism of the drug delivery device.

FIG. 2 shows a cross-sectional view of the drug delivery device showing the drive mechanism 4 in more detail.

The drive mechanism 4 comprises a piston rod that is embodied as a lead screw 14 having a thread 30 and is therefore referred to as lead screw 14 in the following. The lead screw 14 comprises a bearing 15 that abuts the bung 7.

The lead screw 14 is threadedly coupled to a thread insert 16, which may be an integral part of the housing or connected to the housing, e.g. being rigidly constrained into the body 3 or the cartridge holder 5. The latter, itself, is rigidly constrained in the body 3. In an alternative embodiment, the body 3 and the cartridge 5 are releasably connected. Due to the threaded coupling between the thread insert 16 and the lead screw 14, rotational movement of the lead screw 14 with respect to the thread insert 16 causes axial movement of the lead screw 14 with respect to the thread insert 16 and the body 3.

A trigger nut 18 is located proximally with respect to the thread insert 16, the trigger nut 18 being coupled to the lead screw 14 in such a manner that the lead screw 14 is axially moveable and rotational movement with respect to the trigger nut 18 is constrained. The trigger nut 18 is located between the thread insert 16 and an inner wall of the body 3, the wall serving as a socket 62 through which the lead thread 14 runs. The socket 62 is placed proximally to the trigger nut 18 in such a manner that the trigger nut 18 is held in its axial position between the thread insert 16 and the socket 62.

The trigger nut 18 is located in the hole of the sleeve-shaped trigger member 9 that is releasably coupled to it in such a manner that the trigger nut 18 and the trigger member 9 are engaged in a first state, which is a dose setting state of operation. They are disengaged in a second state, which is a drug delivery state or dose delivery state of operation. In the first state, rotational movement between the trigger nut 18 and the trigger member 9 is constrained. In the second state, rotational movement is possible. The trigger 8, in particular the trigger member 9, is elastically deformable, wherein the trigger member 9 is biased in the first state in such a manner that it engages with the trigger nut 18. When the trigger button 10 is pushed towards the trigger member 9, it is deformed, thereby disengaging the trigger member 9 and the trigger nut 18.

The trigger and trigger nut arrangement 8, 18 serves as a locking means being suitable for constraining the rotational movement of the lead screw 14 with respect to the thread insert 16 and housing in the dose setting state. The trigger and trigger nut arrangement 8, 18 serving as a locking means releases the lead screw 14 in the dose delivery state, i.e. the drug delivery state, in such a manner that the lead screw 14 is moveable with respect to the thread insert 16, which allows for distal movement of the lead screw 14 with respect to the thread insert 16 and the housing, thereby delivering the drug. In an alternative embodiment (not shown) the locking means is embodied as a single component that engages with the lead screw 14 in the dose setting state thereby constraining rotational movement between the components. Such locking means may be formed an elastically deformable sleeve that disengages when it is deformed in the dose delivery state.

The drive mechanism 4 further comprises a drive member, which may be formed as a drive sleeve 22 driving the lead screw 14 distally. The lead screw 14 runs through the drive sleeve 22, which is located proximally with respect to the trigger member 9 and the socket 62. The drive sleeve 22 is moveable along the lead screw 14, but rotational movement between the components is constrained. The drive sleeve 22 may be splined to the lead screw 14. If the lead screw 14 is locked, the drive member 22 can move axially with respect to the housing and the lead screw 14. When the lead screw 14 is released, helical movement of the drive member 22 with respect to the housing during the drug delivery state drives the lead screw 14 helically through the thread insert 16.

The drive sleeve 22 comprises a thread 23 located on its outer wall, the thread 23 being suitable for engaging with a thread 25 located on the inner wall of the dial sleeve 24. The dial sleeve 24 is threadedly coupled to the drive sleeve 22 in such a manner that at least the proximal part of the drive sleeve 22 may be screwed into the dial sleeve 24. The dial sleeve 24 is coupled to the proximal end of the body 3 in such a manner that rotational movement between the components is possible. The dial sleeve 24 is coupled to the dial member 11, which may be manually rotated with respect to the body 3 by the user, thereby rotating the dial sleeve 24 as well.

A main spring 20 is located between the body 3 and the dial sleeve and drive sleeve arrangement 22, 24. A spring is an elastic object used to store mechanical energy. The main spring 20 is a compressible torsion spring storing energy when being wound and compressed. Deformation of such a spring may be achieved by means of a helical movement of one spring end with respect to the other end. The main spring is formed as a helical spring. One end 66 (shown in FIG. 3) of the main spring 20 is connected to the dial sleeve 24. The other end 64 (shown in FIG. 3) is connected to the drive sleeve 22. A proximal movement of the drive sleeve 22 with respect to the dial sleeve 24 compresses and winds the main spring 20, thereby loading it. Also, the rotational movement of the drive sleeve 22 with respect to the dial sleeve 24 torques the main spring 20, thereby charging it. When the main spring 20 is released, the drive sleeve 22 moves back, and vice versa.

A number sleeve 26 that is connected with the distal end of the drive sleeve 22 extends along the drive sleeve 22 in such a manner that the main spring 20 is located between the drive sleeve 22 and the number sleeve 26. The number sleeve 26 moves axially with the drive sleeve 22. The movement of the number sleeve 26 may be visible through a window 28, e.g. a cut-out, in the body 3, thereby indicating the value of the set dose as described later.

Figure 3:
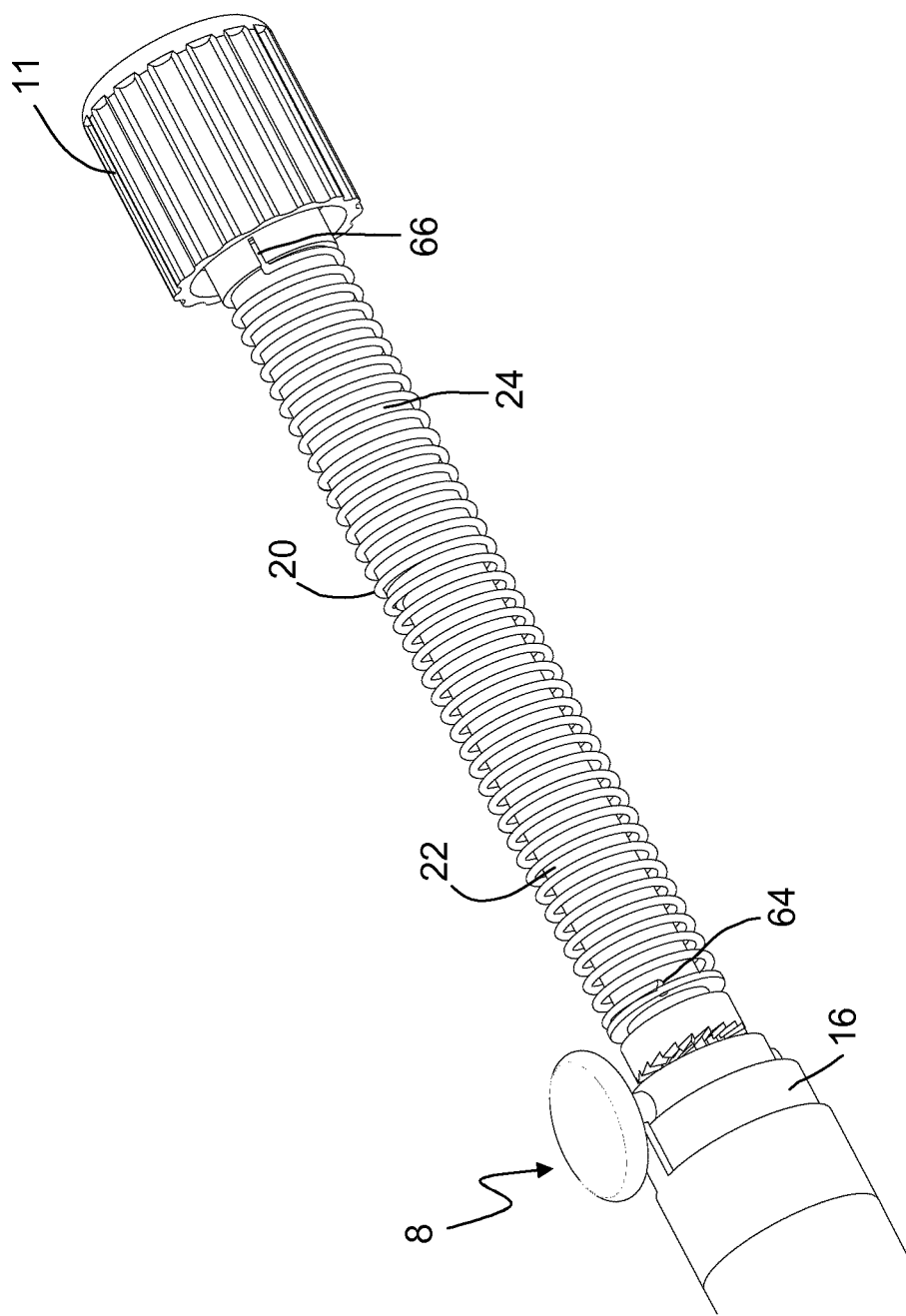
FIGS. 3 and 4 show the drive mechanism, where some components are hidden for the sake of clarity.

FIG. 3 shows the drive mechanism concentrating on the main spring, where the body 3 and number sleeve 16 are hidden for clarity. This figure illustrates the interaction between the dial member 11 and the main spring 20.

The drive mechanism 4 comprises the drive sleeve 22 and the dial sleeve 24, which are threadedly connected in such a manner that the drive sleeve 22 may be partly moved into the dial sleeve 24 by a helical movement. Threadedly connected means that one component has a thread engaging with a thread of the other component, the connection allowing for helical movement of one component with respect to the other.

The main spring 20 helically runs from the distal part of the drive sleeve 22 along the outer side of the drive and dial sleeves arrangement 22, 24 to the proximal end of the dial sleeve 24. The main spring 20 is a torsion spring that is rotationally constrained at one end 66 in the dial sleeve 24 and at the other end 64 in the drive sleeve 22. The end 66 that is connected to the dial sleeve 24 extends in the proximal direction 2 and is placed in a groove in a protruding part of the dial sleeve 24. The spring extension pushes the end 66 in place, thereby fixing the main spring 20. The other end 64 of the main spring 20 is fixed in the same manner to the drive sleeve 22.

During assembly, the main spring 20 is slightly compressed to ensure that it remains in engagement with the rotational constraints in the drive and dial sleeves 22, 24 during operation of the drug delivery device. Also during spring assembly, a number of turns are applied to the main spring 20 to pre-charge it and to ensure that even in the most relaxed condition, i.e. one unit left prior to the end of the dose, the main spring 20 applies a torque sufficient to complete the dose dispense. In other words, the main spring 20 is in compression and torsion during the operation of the device.

The main spring 20 applies a torque between the drive sleeve 22 and the dial sleeve 24. In a so-called "at rest" condition, ie. the trigger 8 is released and zero units are dialled, the torque applied to the drive sleeve 22 is reacted, which means that, even though the main spring 20 implies torque, no movement or drug delivery is caused. This reaction is caused by features that constrain rotational movement of the drive sleeve 22 and dial sleeve 24.

The torque applied to the drive sleeve 22 is reacted by the trigger 8 via the lead screw 14 and the trigger nut 18. The torque applied to the dial sleeve 24 is reacted by the body 3 via ratchet means 53 at the proximal end of the dial sleeve 24, as explained later.

Figure 4:
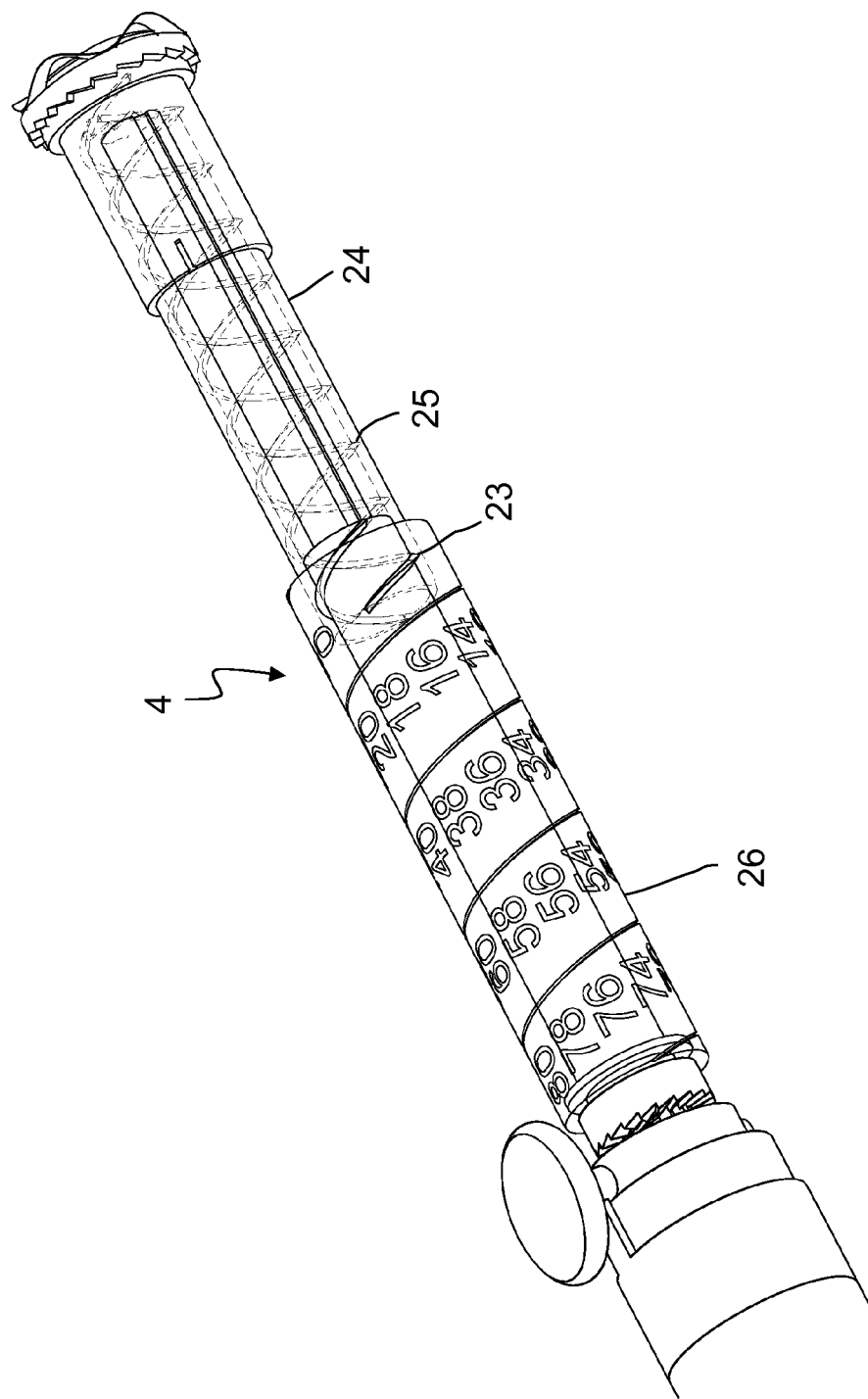

FIG. 4 shows the drive mechanism 4, illustrating the drive sleeve engagements with the dial sleeve 24 and the number sleeve 26. The body 3 is hidden for the sake of clarity.

The drive sleeve 22 is threaded to the dial sleeve 24. The thread 23 of the drive sleeve 22 located on the proximal end of the drive sleeve engages with the thread 25 located on the inner wall of the dial sleeve 24. The thread 23 of the drive sleeve 22 is located inside the dial sleeve 24 in any position of the drive sleeve, which ensures that the outer side of the drive sleeve and dial sleeve arrangement 22, 24 is smooth, thereby preventing the action of the main spring 20 (not shown) from being disturbed by any protrusions on the other side.

The number sleeve 26 is connected with the drive sleeve 22 in such a manner that there is an axial constraint between the components, which means that the number sleeve 26 does not move axially with respect to the drive sleeve 22.

The drive sleeve 22 may transfer the torque from the main spring 20 (not shown) to the lead screw 14 via splines (not shown).

The drug delivery device may be a disposable pen injector for multiple, user-variable dose applications. The force required to set and dispense a dose is consistent and independent of the force required to move the bung 7 within the cartridge 6. The force required to actuate the trigger 8 and the distance which it has to move are small, providing a significant ergonomic advantage, particularly for those users with impaired dexterity. It permits any dose to be selected within a range of zero to a pre-defined maximum. It has a relatively low part count and is particularly attractive for cost-sensitive device applications.

The following figures show several parts of the drug delivery device in more detail.

Figure 5:
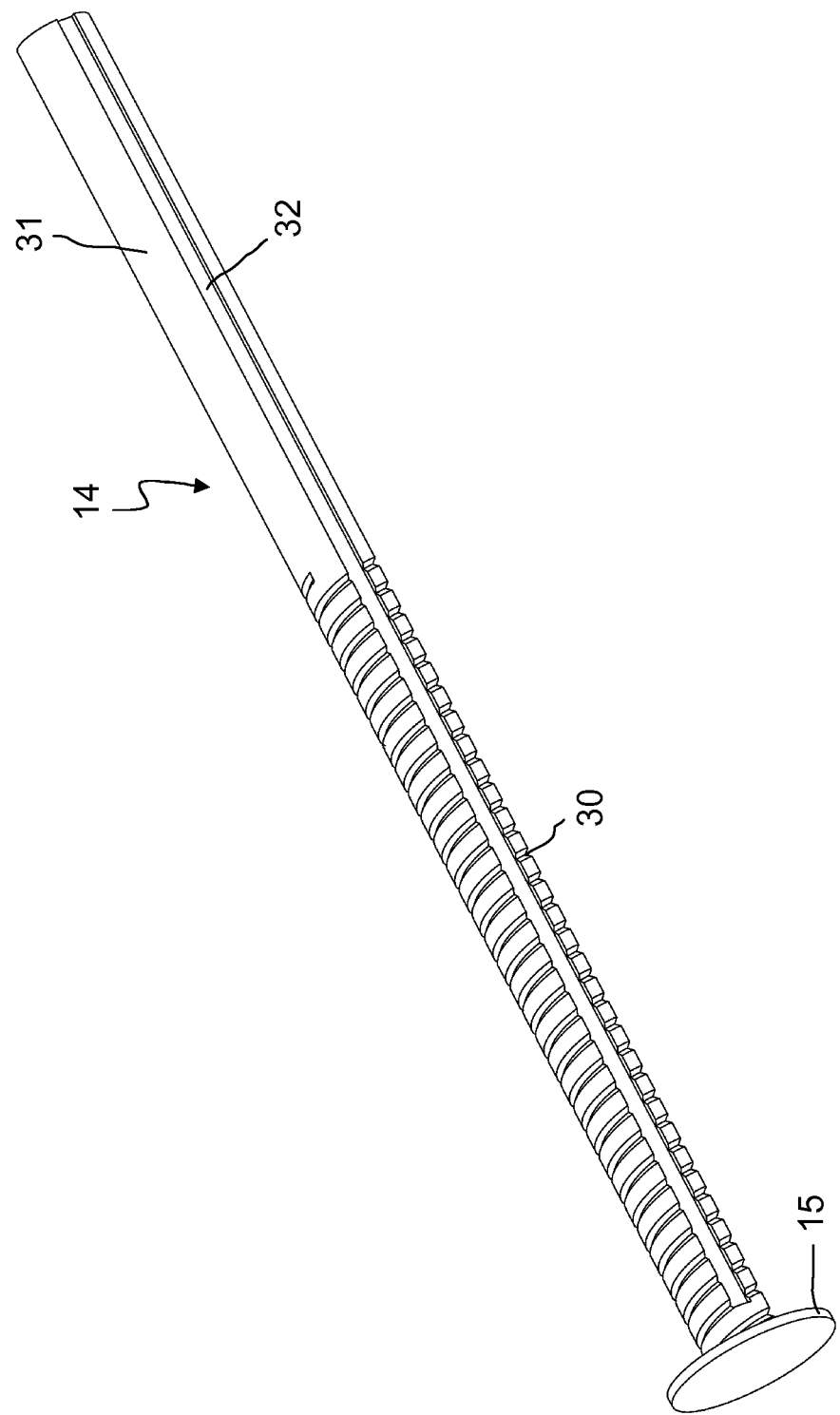
FIG. 5 shows a piston rod of the drive mechanism.

FIG. 5 shows the lead screw 14 including the bearing 15 that forms the distal end of the lead screw 14. The bearing 15 is rotationally moveable with respect to a shaft 31 of the lead screw 14. Axial movement between the parts of the lead screw 14 is constrained. The shaft 31 of the lead screw 14 comprises a thread 30 running from the distal end of the shaft 31 along a part of its length. The thread may be a twin-start thread, comprising two grooves running diametrically opposed and helically along a part of the shaft 31. In an alternative embodiment, the thread may be a single start thread.

Moreover, there are two grooves 32 located on opposite sides of the shaft 31 and running along the axial direction of the lead screw 14. The grooves 32 form a splined connection with splines, e.g. teeth or ridges, of the trigger nut 18 and the drive sleeve 22. In an alternative embodiment, the lead screw 14 has splines connectable to grooves in other components.

The distal face of the bearing 15 abuts the bung 7 of the cartridge 6 (not shown). The lead screw 14 drives the bung 7 distally in order to deliver the drug. This distal movement of the lead screw 14 also includes a rotational movement of the shaft 31 that is decoupled from the bearing 15. In other words, the bearing 15 pushes the bung 7 distally without rotating itself.

Figure 6:
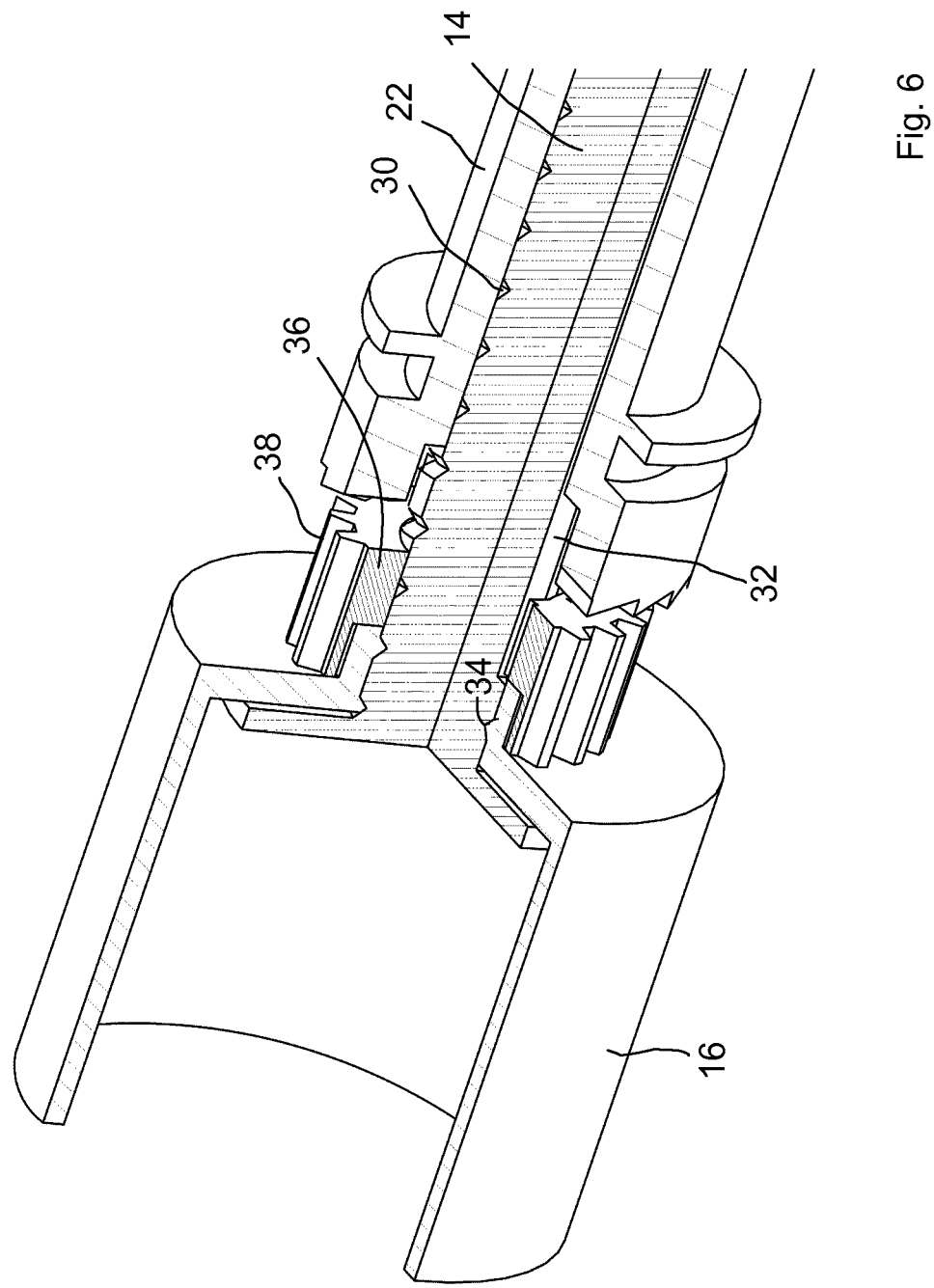
FIG. 6 shows a cut-away view of the distal part of the drive mechanism.

FIG. 6 shows a cut-away view of the distal part of the drive mechanism 4, which shows the lead screw 14 held by the thread insert 16, the trigger nut 18 and the drive sleeve 22. Other components are hidden for the sake of clarity. It should be mentioned that the lead screw 14 and its bearing 15 are shown as a single component, but there are actually two components, as described above.

The cup-shaped thread insert 16 holds the proximal end of the cartridge 6 (not shown). There is a hole in the bottom of the thread insert 16 through which the lead screw 14 runs. A thread 34 located on the side walls of the hole engages with the thread 30 of the lead screw 14. The thread 34 of the thread insert 16 may be formed by protrusions engaging with the grooves of the lead screw thread 30. Alternatively, the thread 30 of the lead screw 14 may be formed by protrusions and the thread 34 of the thread insert 16 may be formed by grooves. Rotational movement of the lead screw 14 with respect to the thread insert 16 causes axial movement of the lead screw 14 with respect to the thread insert 16.

The trigger nut 18 is positioned at the proximal end of the thread insert 16. There is a multitude of radially extending teeth 38 formed by the sidewall of the trigger nut 18, the teeth 38 being arranged in a toothed-wheel manner. The lead screw 16 runs through the trigger nut 18, both components being coupled in such a manner that axial movement with respect to one another is possible but rotational movement with respect to one another is not. The components are splined, which means that radially inwards extending protrusions or splines 36 of the trigger nut 18 engage with the grooves 32 of the lead screw 14. The same effect may be achieved by any non-rotation-symmetric cross-section of the lead screw 14 corresponding to the non-rotation-symmetric cross-section of the hole in the trigger nut 18.

The lead screw 14 also runs through the drive sleeve 22 that is located proximally with respect to the trigger nut 18. The lead screw 14 and the drive sleeve 22 are coupled in such manner that axial movement with respect to one another is possible but rotational movement with respect to one another is not. The components are also splined.

Figure 7:
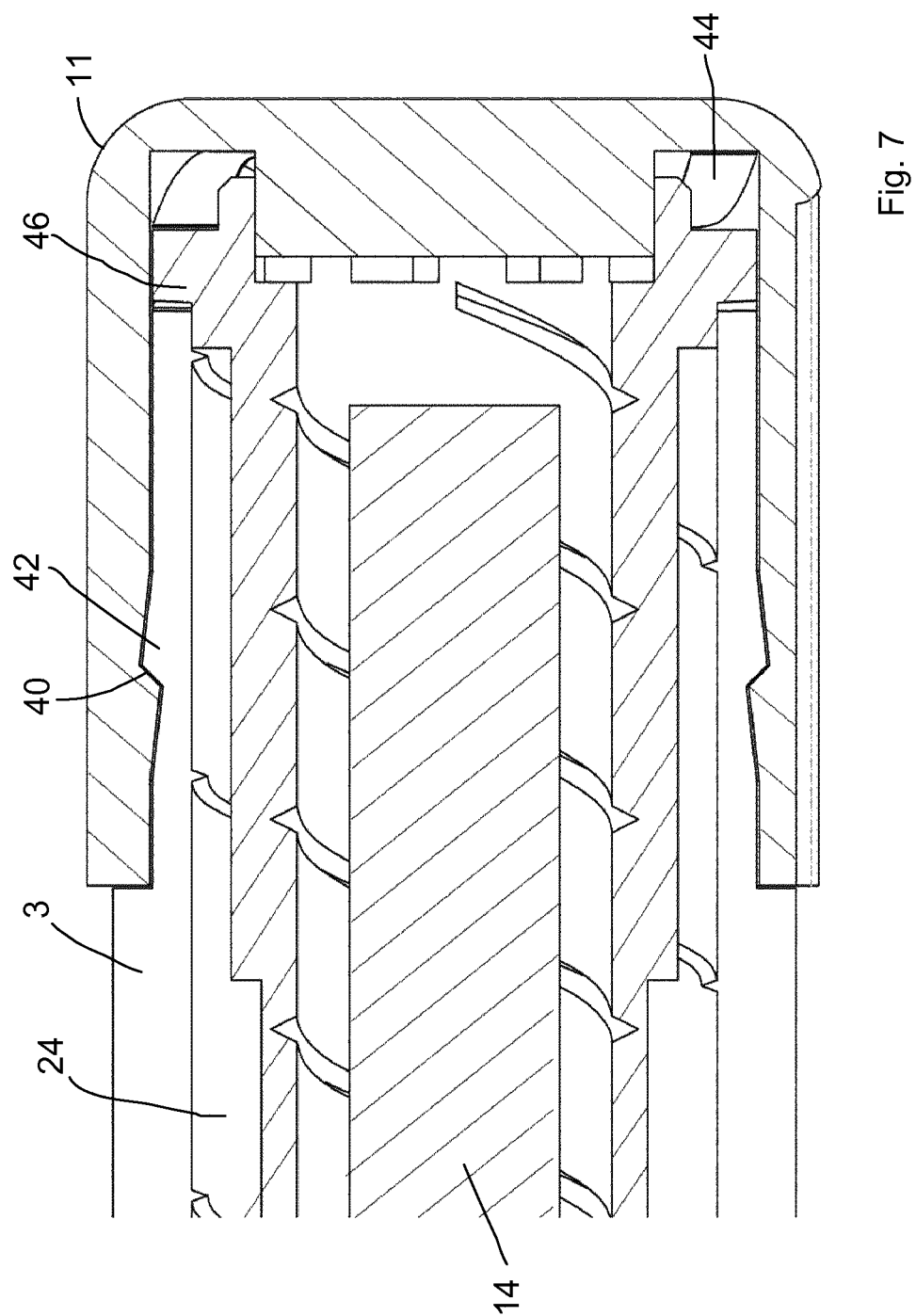
FIG. 7 shows a cross-sectional view of the proximal part of the drug delivery device.

FIG. 7 illustrates the dialling mechanism and shows a cross-sectional view of the proximal part of the drug delivery device that includes the dial member 11. The dial member 11 is a sleeve whose proximal end is closed. It is located at the very proximal end of the drug delivery device. Side parts of the dial member 11 extend over the proximal end of the body 3. The dial member 11 is rotationally moveable with respect to the body 3. A circumferentially protruding step 40 having a triangular cross-section and being located on the inner wall of the side part snaps over a circumferentially protruding step 42 having a triangular cross-section and being located on the outer wall of the body 3. The dial member 11 is not axially moveable with respect to the body 3, but free to rotate. Alternative embodiments of the connection between the dial member 11 and the body 3 may be possible, e.g. a circumferential protrusion or several protrusions that may have a rectangular or semicircle cross-section engaging with a circumferential groove.

The dial sleeve 24 is located inside the body 3. The proximal end of the dial sleeve 24 is formed as a flange 46 extending radially over the proximal face of the body wall, thereby preventing distal movement of the dial sleeve 24. A spring disc 44 is located between the proximal face of the flange 46 and the internal closed face of the dial member 11. The spring disc 44 ensures that the dial sleeve 24 is pushed towards the body 3 and away from the dial member 11 until the steps 40, 42 engage with each other. Thus the spring disc 44 avoids axial clearance between the dial member 11, the dial sleeve 24 and the body 3.

The user sets and unsets a dose by means of rotating the dial member 11 with respect to the body 3. Clockwise rotation 12 of the dial member 11 increases the dose set. Counter-clockwise rotation 13 of the dial member 11 decreases the dose set.

Figure 8:
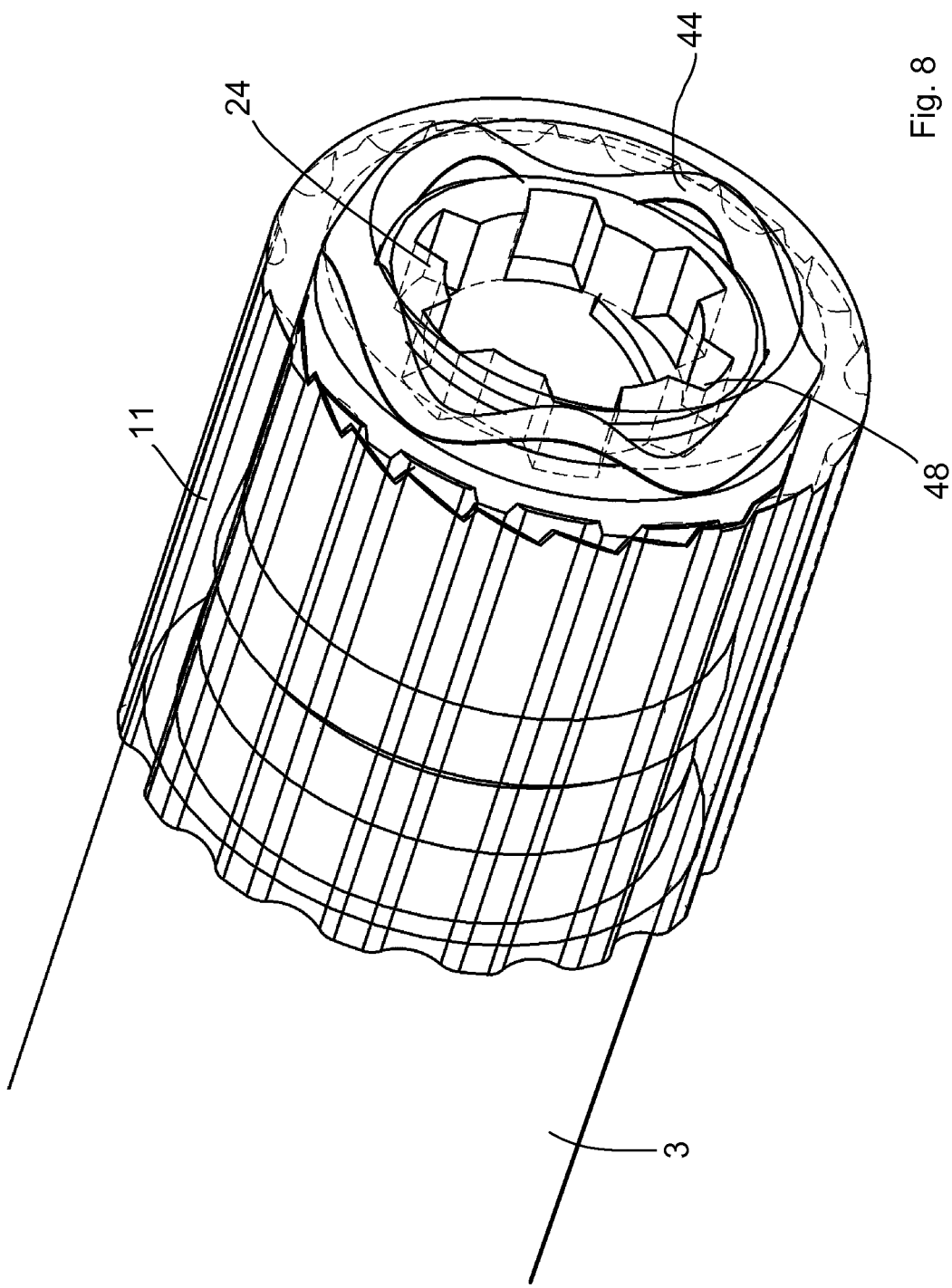
FIGS. 8 and 9 show the proximal end of the drug delivery device.

FIG. 8 provides a view of the proximal end of the drug delivery device. There are splines 48, which are located on the inside bottom of the dial member 11 and extend in the distal direction 1, the splines 48 engaging with a corresponding cavity of the dial sleeve 24 to transfer rotational movement to the dial sleeve 24 and user-applied torque via the dial sleeve 24 to the main spring 20 (not shown).

Figure 9:
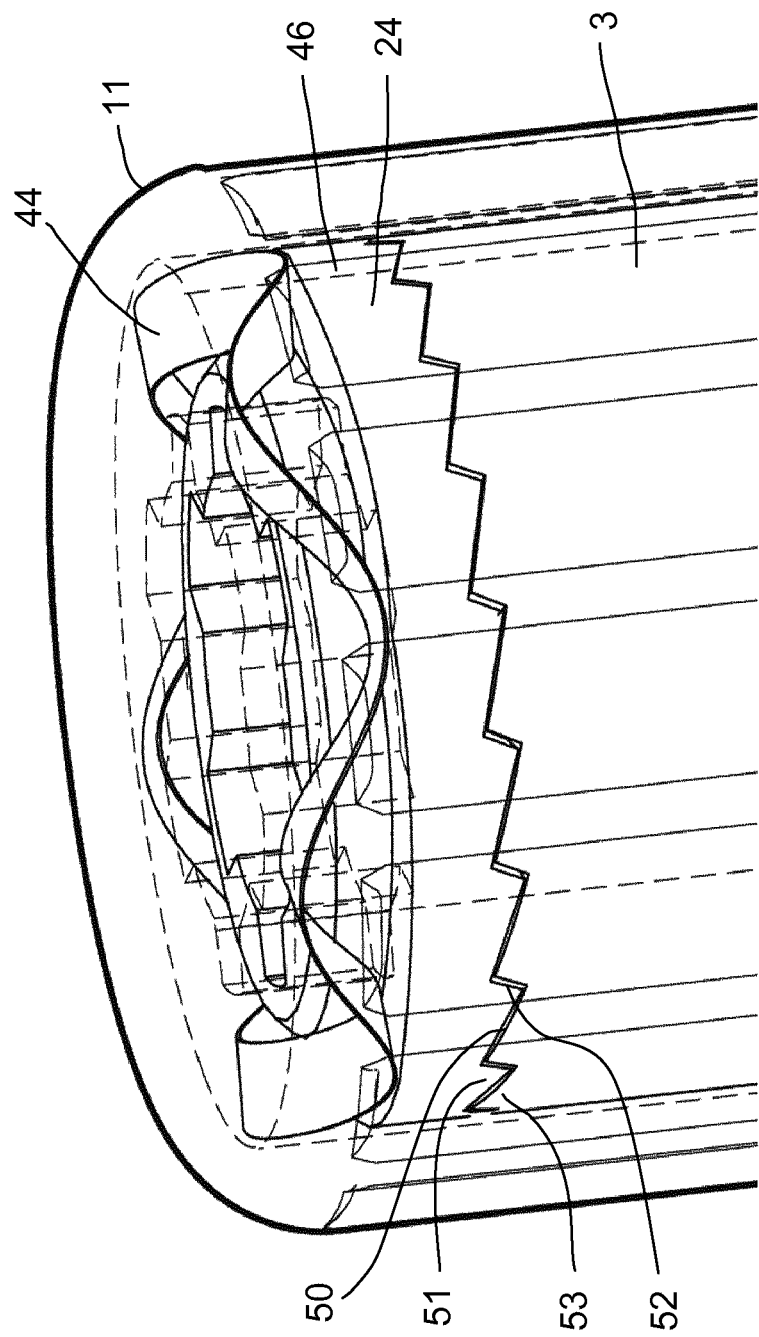

FIG. 9 shows a semi-transparent side-view of the proximal end of the drug delivery device. The distal face of the flange 46 of the dial sleeve 24 is serrated and engaging with the corresponding serrated proximal face of the body 3, thereby forming engaging dialling ratchet means 51, 53. The distal face comprises alternating shallow dialling-up ramps 50 and steep dialling-down ramps 52 serving as a dialling ratchet means. The proximal face of the body 3 has corresponding teeth.

The spring disc 44, being a compression wave spring, serves as a ratchet spring that acts between the dial member 11 and the dial sleeve 24 to maintain the engagement of the dialling ratchet means 51, 53.

The spring disc force, the ratchet teeth ramp angles and coefficient of friction define the torque required to overhaul the ratchet. The ramp angle of the ratchet in counter-clockwise direction 13 is steeper than that in the clockwise direction 12, so that the torque required to overcome the ratchet when dialling up against the torque of the main spring 20 is lower than when dialling down a dose.

When dialling up in the clockwise direction 12, the required user torque is the sum of the torque to charge the main spring 20 and the torque to overhaul the ratchet teeth. When dialling down in the counter-clockwise direction 13, the main spring 20 assists the user in overhauling the ratchet teeth. The dialling-down ramp 52 angles are designed to ensure that the torque from the main spring 20 alone is not sufficient to overhaul the ratchet teeth in any state of dialling. However, the addition of user-applied torque, in the dial-down direction, supplements the main spring torque and is sufficient to dial the device down. The relative ramp angles are designed to require similar user input torques to dial up and to dial down when the torque from the main spring 20 is accounted for. Since the main spring torque changes with dialling, the user torque may be matched at zero units, which means at maximum dose set, the main spring torque is greater and, therefore, the dial-up torque is greater than the dial-down torque. An alternative embodiment may match the dialling torques at some other dialled dose position, between zero units and maximum dose set positions.

The dialling ratchet means 51, 53 may have a feedback function, which means e.g. during operation they emit a clicking noise, thereby providing audible feedback. Alternatively or additionally there may be visual or tactile feedback. Such feedback functions may be provided by the interaction of other components of the device.

Figure 10:
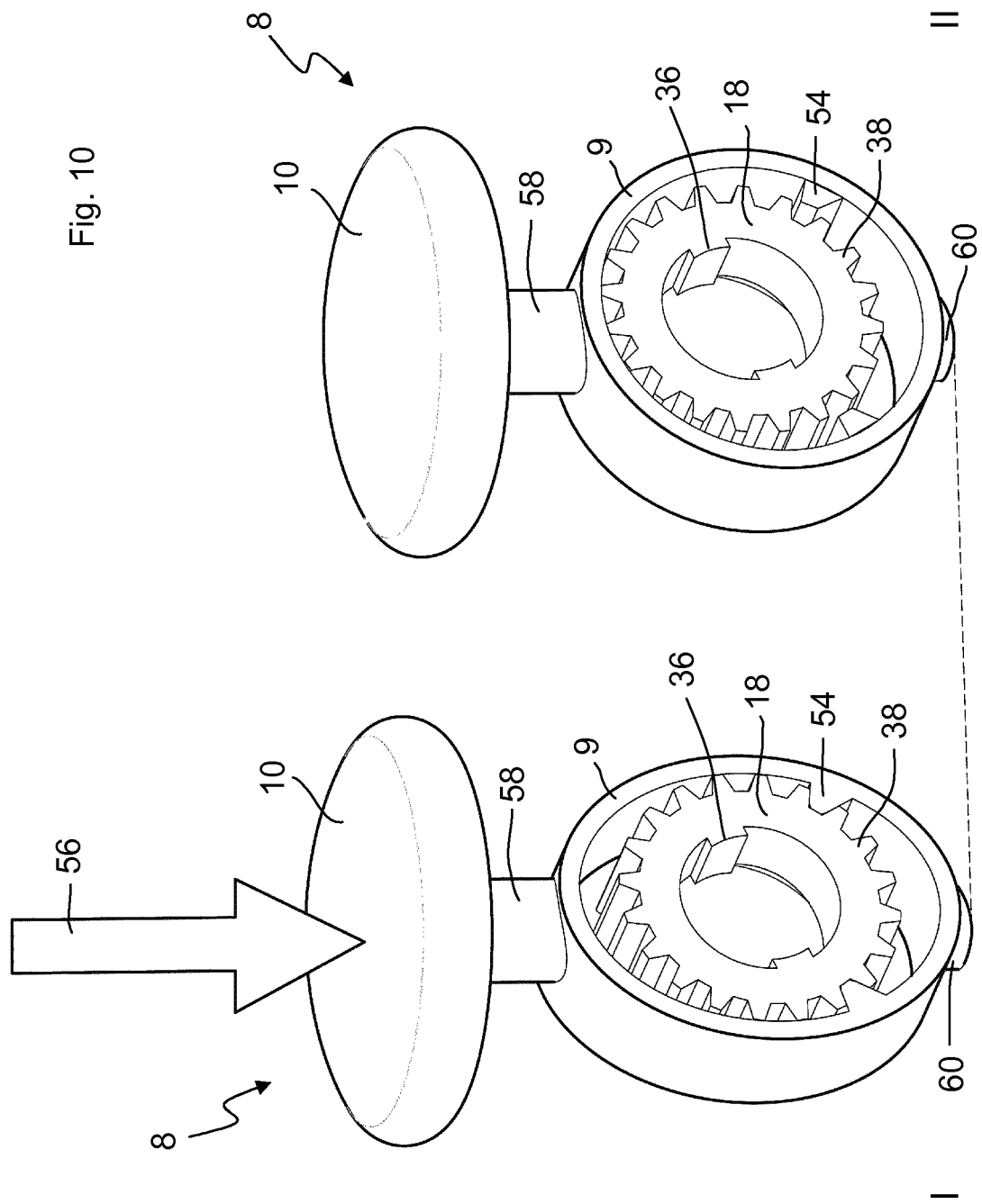
FIG. 10 shows an embodiment of a trigger nut and an embodiment of a trigger.

FIG. 10 shows the trigger nut 18 and the trigger 8 comprising the trigger member 9 and the trigger button 10 in a first state, which is indicated by I, and a second state, which is indicated by II:

The trigger member 9 is a sleeve-shaped element that is made in one piece with the trigger button 10 and a boss 58 connecting the trigger member 9 and the trigger button 10. The trigger 8 is made totally or partly of an elastically deformable material, e.g. plastics. Thus, the trigger member 9 is elastically deformable, which means that the trigger member 9 may be deformed by applying a force and returns to its original shape after the force that caused the deformation is no longer applied. The trigger member 9 serves as a locking means being suitable for constraining rotational movement of the lead screw 14 (not shown) with respect to the thread insert 16 (not shown) in a dose setting state.

The trigger 8 comprises bosses 58, 60 that may be protrusions extending radially outwards. The first boss 58 connects the trigger member 9 and the trigger button 10. The first boss 58 extends through the housing (not shown) from the trigger member 9 located inside the housing to the trigger button 10 located outside the housing. A second boss 60 is located on the opposite side of the trigger member 60, the second boss 60 being suitable for being connected with the housing, e.g. by a force-fit connection, when the second boss is pressed into a cavity of the housing.

The trigger member 9 is deformed by the force applied by the user to the trigger button 10 and the reacting or counter-acting force applied by the second boss 60 connected with the housing the trigger member 9 is pushed to. An alternative embodiment (not shown) may have only the first boss 58 located between the trigger member 9 and the trigger button 10. In this case, the trigger member 9 is pushed towards the housing when pushing the trigger button 10, thereby applying the deforming forces. Another embodiment (not shown) may have more than two bosses located on the outer side of the trigger member 9.

Protrusions or splines 54 are located on the inner side of the trigger member 9. They are preferably not located at the same place where the bosses 58, 60 are located, but in the area which is between the bosses 58, 60. In other words, the protrusions 54 are located beyond the direction of the user-applied deforming force, which runs through the bosses 58, 60. In one embodiment (not shown), a protrusion 54 is centred between the first and second bosses 58, 60. In this embodiment, both protrusions 54 are placed closer to the second boss 60 than to the first one 58.

The trigger nut 18 has an opening suitable for allowing axial movement of the lead screw 14 (not shown) but constraining rotational movement of the lead screw 14. There are splines 36 engaging with the grooves 32 in the lead screw 14. The radial outside of the trigger nut 18 is shaped like a toothed wheel comprising a plurality of teeth 38. The teeth 38 are shaped such that the protrusions 54 of the trigger member 9 may engage with them, thereby constraining rotational movement of the trigger nut 18 with respect to the trigger member 9.

The trigger nut 18 is axially constrained between a flange of the body 3, i.e. the socket 62 (not shown), and the thread insert 16 (not shown). Rotation of the trigger nut 18 controls rotation of the lead screw 14 and, therefore, the axial position of the lead screw 14 relative to the thread insert 16 due to the threaded connection between these components 14, 16.

The trigger member and trigger button assembly 9, 10 is both axially and rotationally constrained in the body 3 and/or the cartridge holder 5. The trigger member and trigger button assembly 9, 10 is compliant in a direction perpendicular to the lead screw axis and in compression only, which is the trigger activation direction indicated by arrow 56. The trigger member 9 is biased to return to the uncompressed state when no force is applied by the user to compress it.

In the uncompressed state as indicated by I, the protrusions 54 of the trigger member 9 engage with the trigger nut 18, rotationally constraining the trigger nut 18. Since the trigger member 9 is rotationally and axially constrained, the constraining trigger nut 18 also prevents rotational movement of the lead screw 12, which also prevents its axial movement.

In the uncompressed state, the trigger member 9 may have a circular or elliptic cross-section. In the latter case, the major or longer axis of the ellipse runs through the bosses 58, 60, or the major axis is closer to them than the minor axis. The distance between points whose midpoint is at the centre of the ellipse is maximum along the major axis, and a minimum along the perpendicular minor axis.

FIG. 10 part II shows the deformed trigger member 9. When a force is exerted on the trigger button 10, it is pushed radially inwards, thereby deforming the trigger member 9 in such a manner that an elliptic cross-section of the trigger member 9 becomes circular or that the minor axis of the ellipse runs through the bosses 58, 60 or the minor axis is closer to them than the major axis. A circular cross-section of the trigger member 9 becomes elliptic in such a manner that the minor axis of the ellipse runs through the bosses 58, 60 or the minor axis is closer to them than the major axis. This deformation causes the splines 54 to move away from the trigger nut's teeth 38, thereby disengaging from the trigger nut 18 and allowing rotation of the trigger nut 18, the lead screw 14 and the drive sleeve 22.

Figure 11:
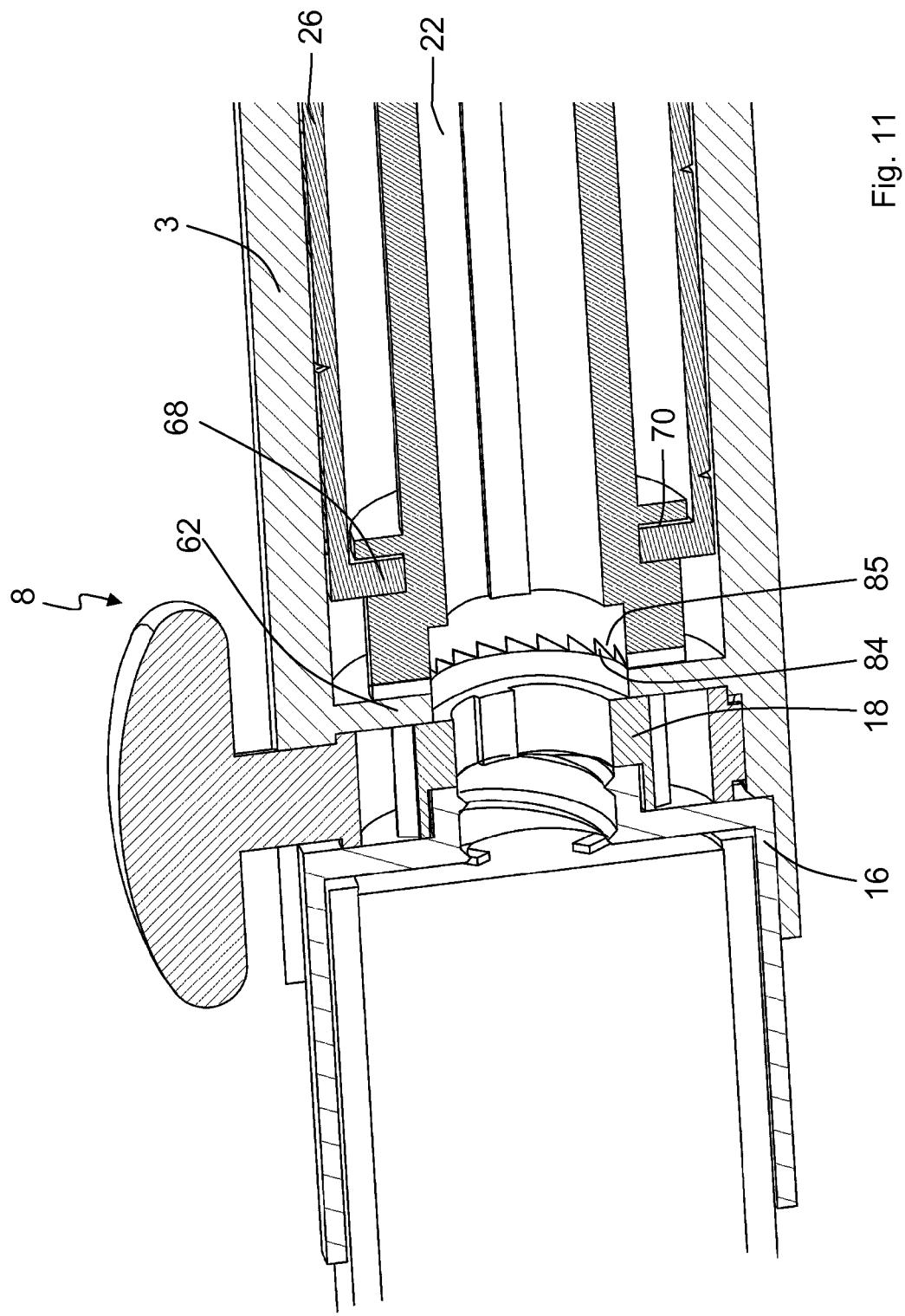
FIG. 11 shows a cross-sectional view of a middle section of the drug delivery device.

FIG. 11 shows a cross-sectional view of a middle section of the drug delivery device, including the trigger nut 18 and the distal part of the drive sleeve 22. The drug delivery device is in an end-of-dose condition, i.e. the end state of dose delivery. A part of the housing that may be an integral part of the body 3 forms the inner wall serving as the socket 62 through which the lead screw 14 runs. The socket 62 is placed proximally to the trigger nut 18 and holds its axial position. On the proximal face of the socket 62 there are ratchet means comprising a multitude of teeth 84 arranged circumferentially. The teeth 84 engage with a ratchet means 85 comprising a multitude of teeth 86 located on the distal face of the drive sleeve 22. The ratchet means 85 serves as an end-of-dose stop, which constrains the movement of the drive sleeve 22 after drug delivery.

The teeth 84, 86 are uniform but asymmetrical, with each tooth having a moderate slope on one edge and a much steeper, preferably axially running slope on the other edge. The connection allows rotary motion in only one direction, where the edges with moderate slopes slide along each other, while preventing motion in the opposite direction, where the edges having steep slopes are pushed against each other.

When a dose is set, the drive sleeve 22 is moved proximally. When the dose is delivered, the drive sleeve 22 moves backwards distally rotating in the clockwise direction 12 until the teeth 84, 86 of the ratchet means engage. In this "at rest" condition, the ratchet means 85 on the distal face of the drive sleeve 22 contacts the teeth 84 on the socket 62, which prevents further movement of the drive sleeve 22. This is the end-of-dose condition.

FIG. 11 also shows the connection between the drive sleeve 22 and the number sleeve 26, the latter comprising an inwardly extending flange 68 located at its distal end. The flange 68 engages with a circumferential groove 70 in the outer wall of the distal part of the drive sleeve 22. This connection constrains axial movement of the number sleeve 26 with respect to the drive sleeve 22.

Figure 12:
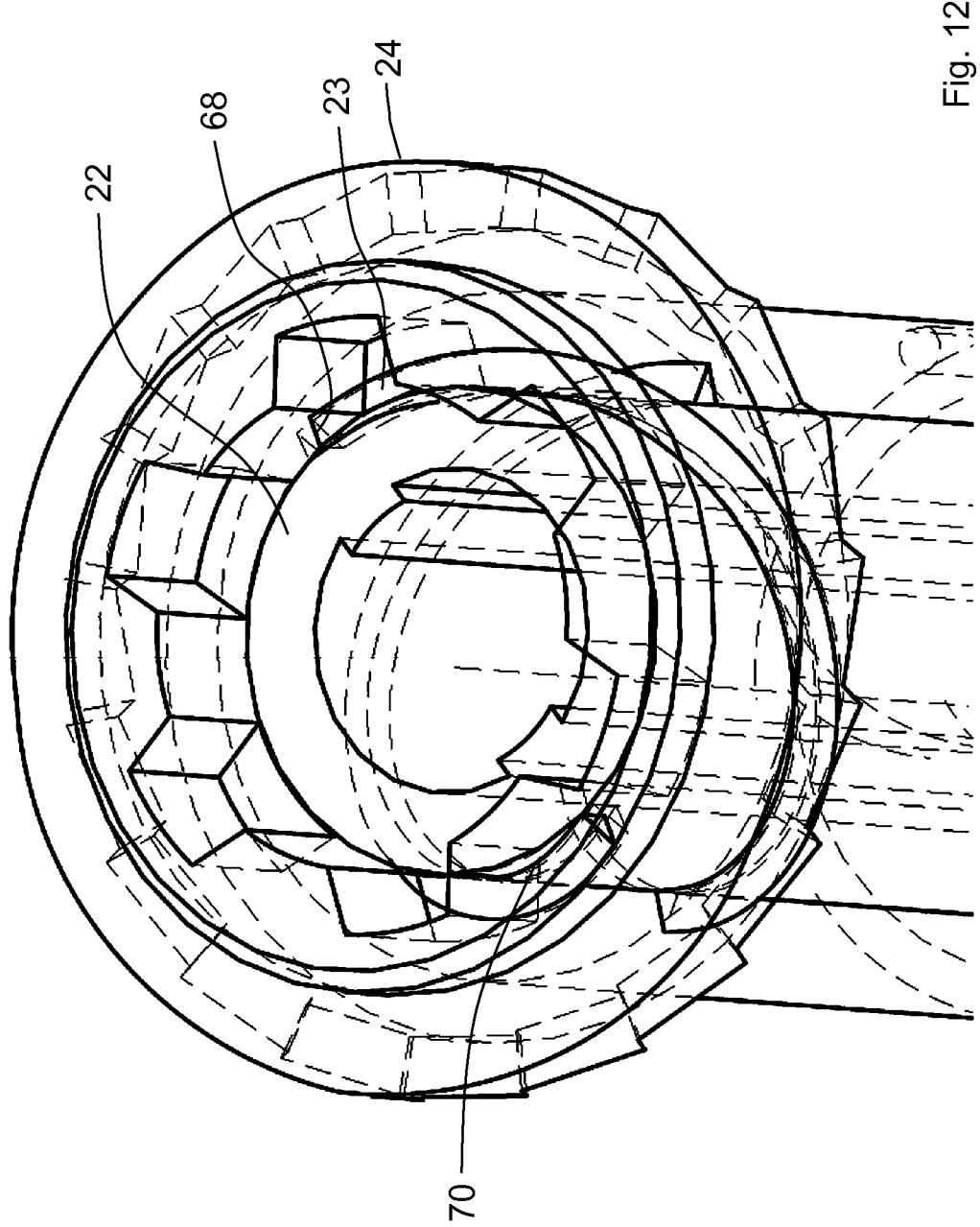
FIG. 12 shows the proximal part of the drug delivery device.

FIG. 12 shows the proximal part of the drug delivery device, where the dial member 11 is hidden for the sake of clarity. FIG. 12 illustrates the maximum-dose condition.

There are means for stopping the proximal movement of the drive member 22 along the dial sleeve 24. There is a stop means 68 within the dial sleeve 24 abutting the ends of the threads 23 on the drive sleeve 22 to limit the axial travel of the drive sleeve 22 and the rotation of the drive sleeve. The means for stopping the proximal movement may include stop faces of the drive sleeve 22 and/or the dial sleeve 24 that may be formed as radial protrusions or flanges abutting each other when the maximum axial movement of the drive sleeve 22 is achieved, i.e. the maximum dose is set.

The benefit of a radial stop means is that such a stop means is more accurate, stronger and stiffer than an axial stop. There is no self-locking effect due to interlocking.

Figure 13:
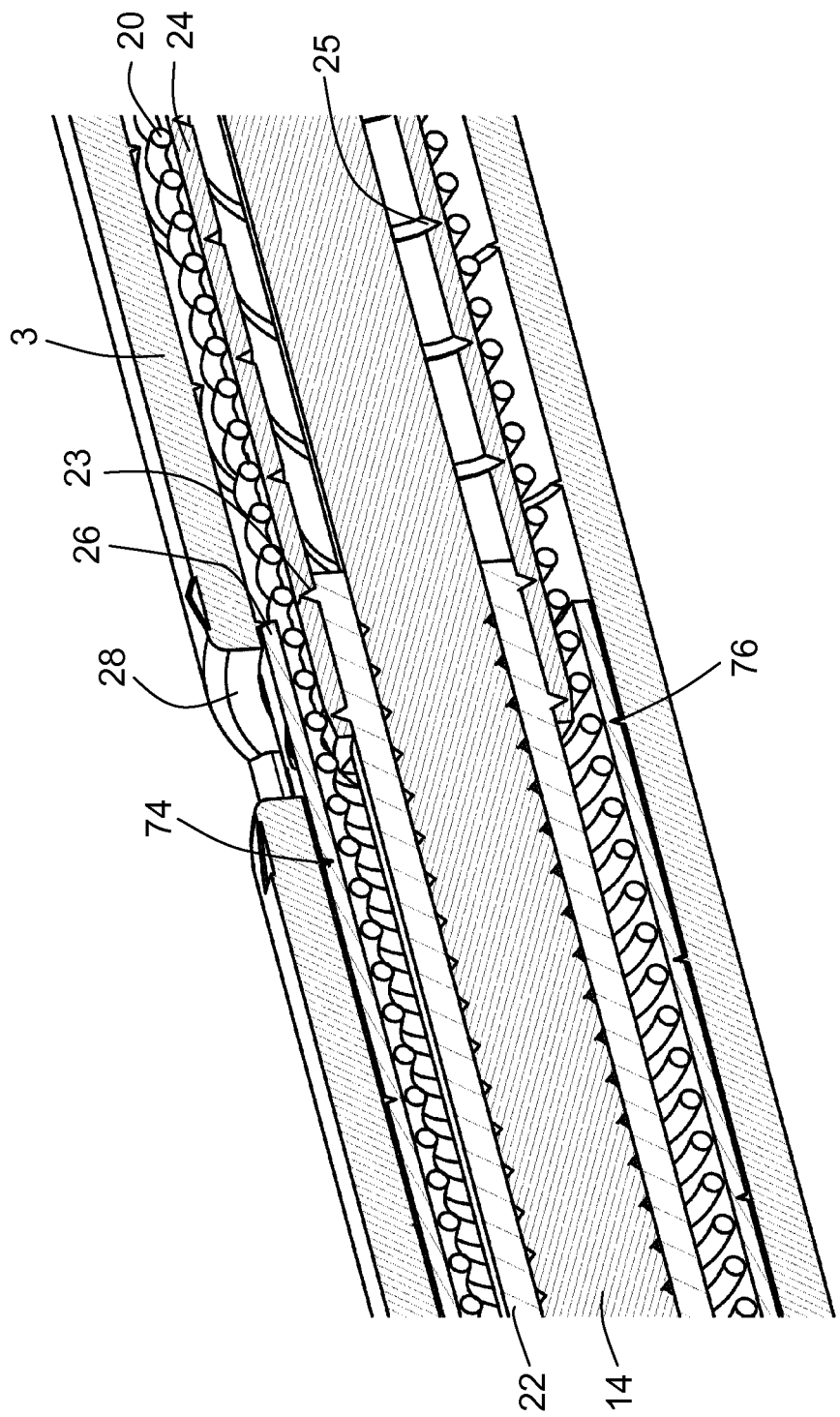
FIG. 13 shows a cross-sectional view of a part of the drug delivery device having a dose display.

FIG. 13 shows a cross-sectional view of a part of the drug delivery device. FIG. 13 illustrates the dose display that is formed by a window 28, e.g. a cut-out, in the body 3 and the number sleeve 26, the window 28 allowing part of the number sleeve 26 to be seen. The number sleeve 26 comprises a thread 76 that is engaged with a thread 74 located on the inner wall of the body 3. The number sleeve 26 is threaded to the body 3 and axially coupled to the drive sleeve 22 so that the axial translation of the drive sleeve 22 results in a rotation and axial translation of the number sleeve 26.

The position of the number sleeve 26 depends on the position of the drive sleeve 22, the latter itself depending on the set dose. Thus, the position of the number sleeve 26 with respect to the window 28 depends on the dose set, the visible part of the number sleeve 26 indicating the dose set.

Figure 14:
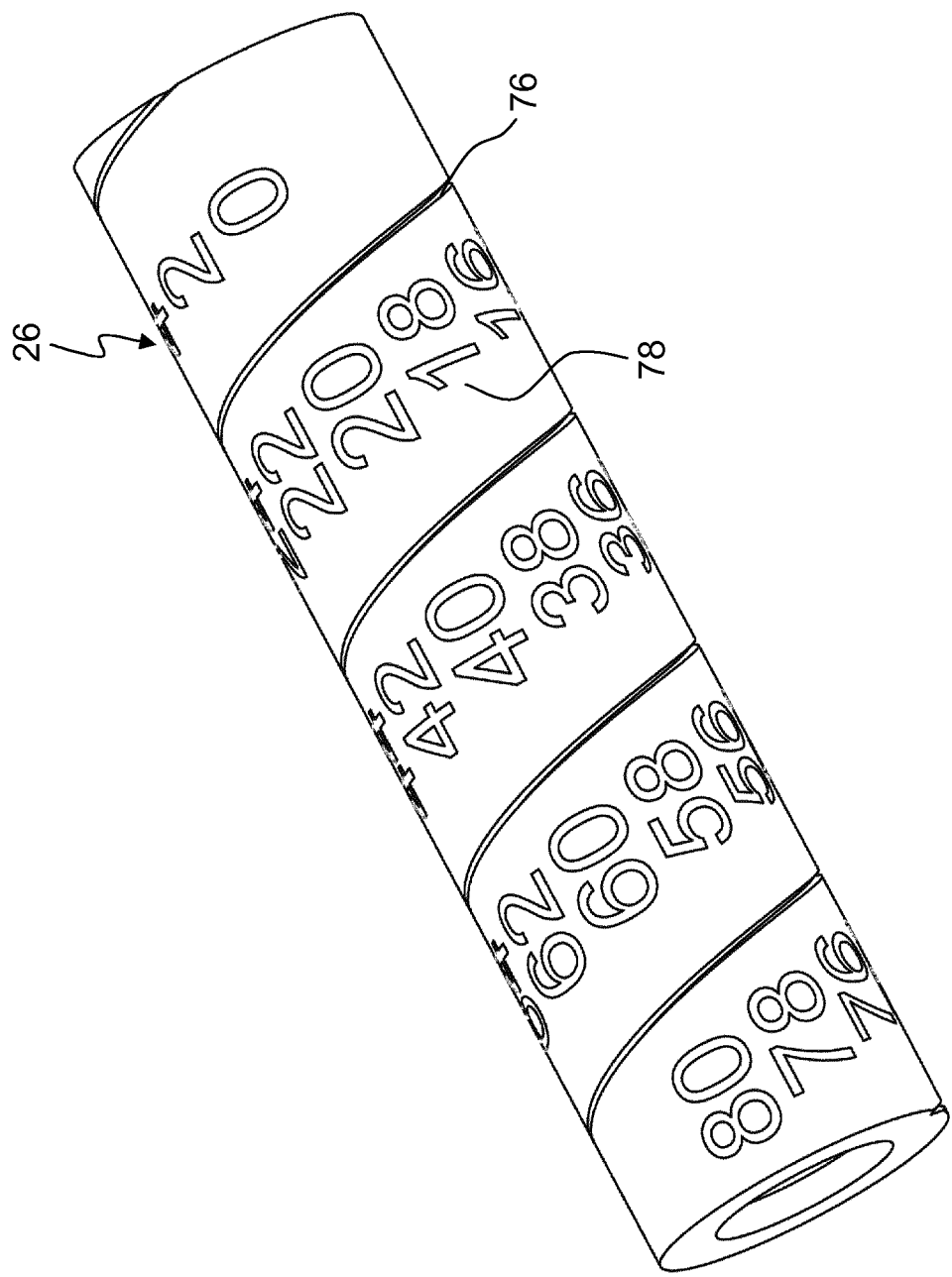
FIG. 14 shows an embodiment of a number sleeve.

FIG. 14 shows the number sleeve 26 that comprises the thread 76 formed by a helical groove. A helically running path of numbers 78 indicating possible values of the set dose is provided on the number sleeve 26. The minimum dose "0" is located at the proximal end. The maximum dose, "80" in this embodiment, is located at the distal end. The maximum may be another value. The value may be smaller or larger than 80. Alternatively, a path of symbols may be provided.

The pitch of the helix of the path of numbers 76 matches the pitch of the thread 76 connecting the number sleeve 26 and the body 3. When a dose is set, the number sleeve 26 helically moves along the body 3, where the value of the dose set, i.e. the respective number on the number sleeve 26, is visible in the window 28.

Figure 15:
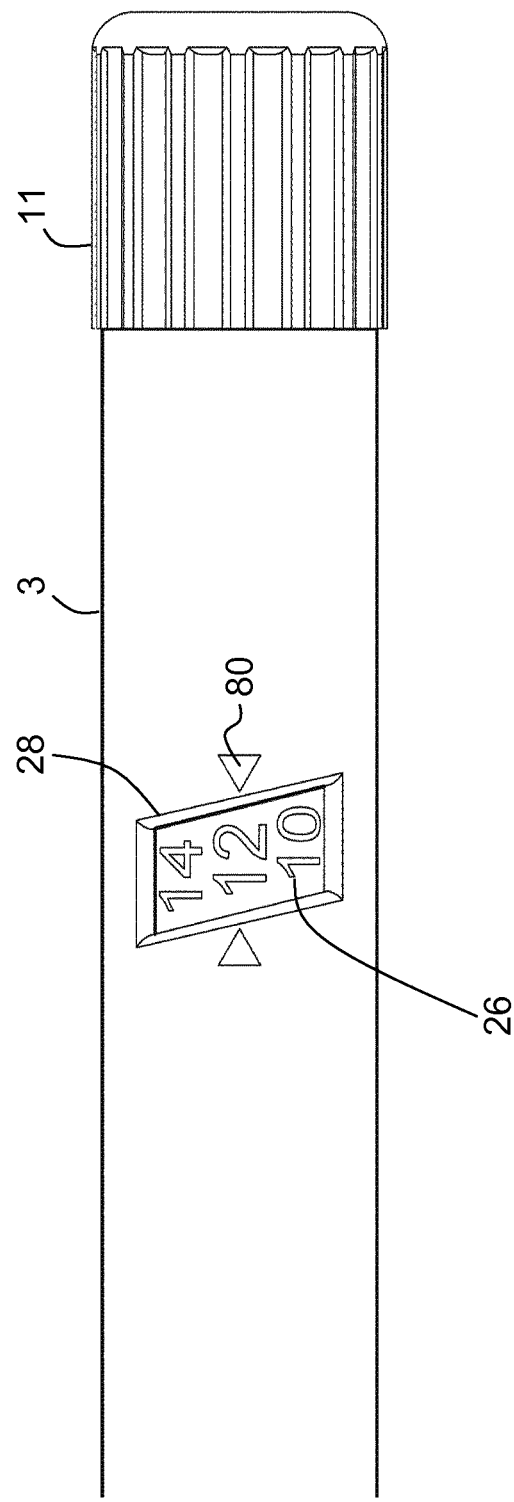
FIG. 15 shows a side view of the proximal part of the drug delivery device.

FIG. 15 shows the proximal end of the drug delivery device with the window 28 in the body 3 and the number sleeve 26 that is visible through a window cut in the body 3. A window cover may be provided for dirt protection for example. In one embodiment the window cover may support holding the number sleeve 26. Such a window cover may be formed as a lens for enlarging the visible numbers on the number sleeve 26. The number that is visible through the centre of the window 28 in the body 3 between the markers 80 corresponds to the dose set. A single number on either side of the dose set display is also visible to aid in determining the subsequent dose. During dose setting, the user rotates the dial member 11 until the desired dose is visible in the centre of the window 28.

The following figures illustrate setting and delivering a dose.

Figure 16:
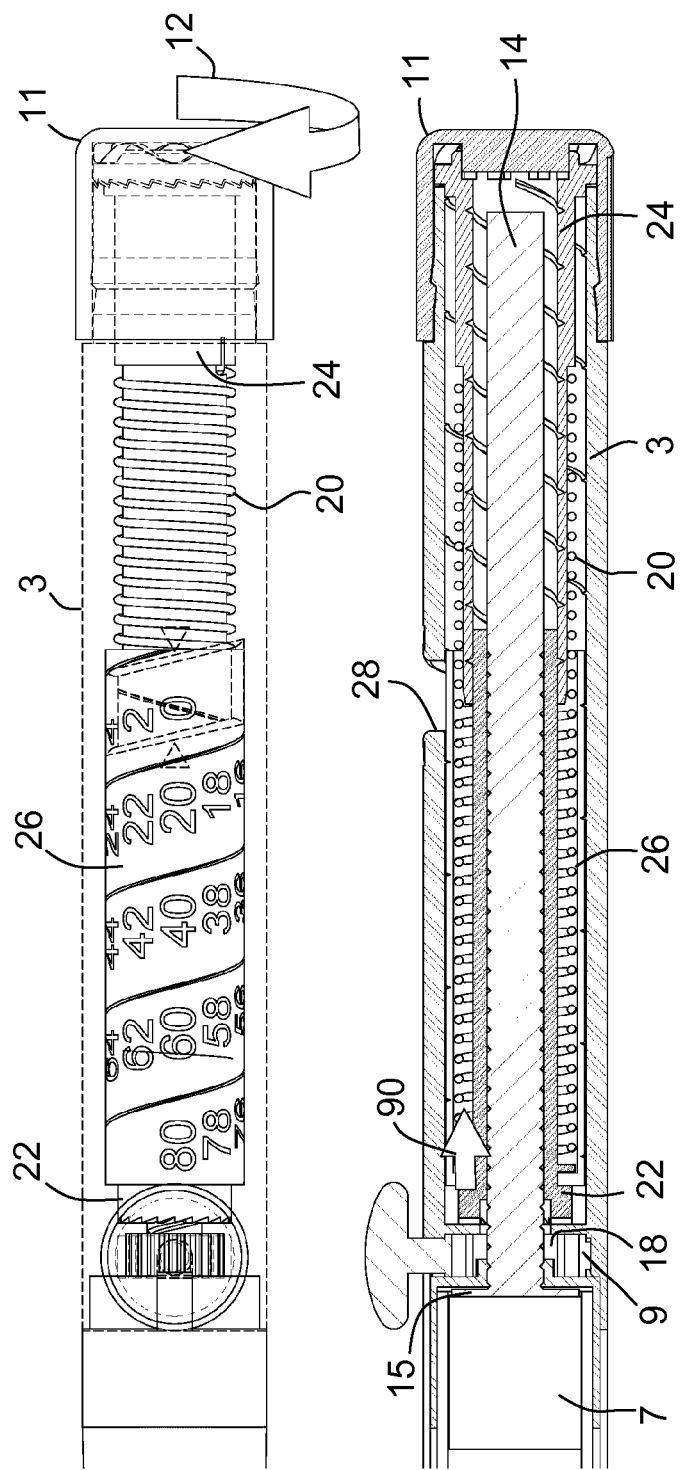
FIG. 16 show the inner components and a cross-sectional view of the drive mechanism of the drug delivery device in a state ready for setting the first dose.

FIG. 16 shows a view (top) and a cross-sectional view (bottom) of the drive mechanism of the drug delivery device in a state ready for setting the first dose.

Before setting and delivering the first dose, the bung 7 is located at the proximal end of the cartridge 6. The bearing 15 abuts the bung 7. In one embodiment there might be a slight distance between the bearing 15 and the bung 7 before first use. In such an embodiment the bearing 15 abuts the bung 7 after a safety shot or priming. The trigger nut 18 is fixed by the trigger member 9, thereby constraining rotation of the trigger nut 18 and the lead screw 14, which is in splined connection with the trigger nut 18. The drive sleeve 22 is in its very distal position with respect to the body 3, where the teeth 84, 86 of the drive sleeve 22 and the socket 26, which serve as end-of-dose stops, are in engagement. The number sleeve 26 is in its very distal position. The number "0", which indicates that no dose is set, is visible through the dose window in the body 3.

When setting a dose, the dial member 11 is rotated by the user in the clockwise direction 12 with respect to the body 3, which rotates the dial sleeve 24 in the same direction. The drive sleeve 22 is drawn in the proximal direction via the thread to the dial sleeve 24. Since the trigger member 9 is uncompressed, it locks the trigger nut 18 and constrains rotational movement of the trigger nut 18. The drive sleeve 22, which is splined to the lead screw 14, is rotationally fixed by the trigger nut 18 via the splined connection between the lead screw 14 and the trigger nut 18. As the dial sleeve 24 is rotated with respect to the drive sleeve 22, the drive sleeve 22 moves only axially, without rotation, with respect to the housing along the lead screw 14 as indicated by arrow 90, thereby charging the main spring 20 in torsion and compression.

The ratchet means 51, 53 between the dial sleeve 22 and the body 3 prevent the main spring 20 from unwinding the dial sleeve 24 when the dial member 11 is released by the user. Furthermore, the ratchet means 51, 53 provide feedback for each set unit as the dose set is increased. When the teeth of the ratchet means 51, 53 slide over their top, the user senses a slight torque variation. Audible feedback may be provided by a clicking sound.

The number sleeve 26 is rotated and translated via the thread to the body 3 as the drive sleeve 22 translates in the proximal direction 2, whereby the number sleeve 26 moves helically in the proximal direction during dose setting. The number sleeve 26 visible through the window 28 in the body 3 displays the dose set to the user. The user may rotate the dial member 11 until the desired dose set is achieved and the respective value is shown in the window 28.

If the user continues increasing the selected dose until the maximum dose limit is reached, the drive sleeve 22 engages with its maximum dose abutment on the thread 23 with the dial sleeve 24, preventing further clockwise rotation 12 of the dial sleeve 24 and dial member 11.

Figure 17:
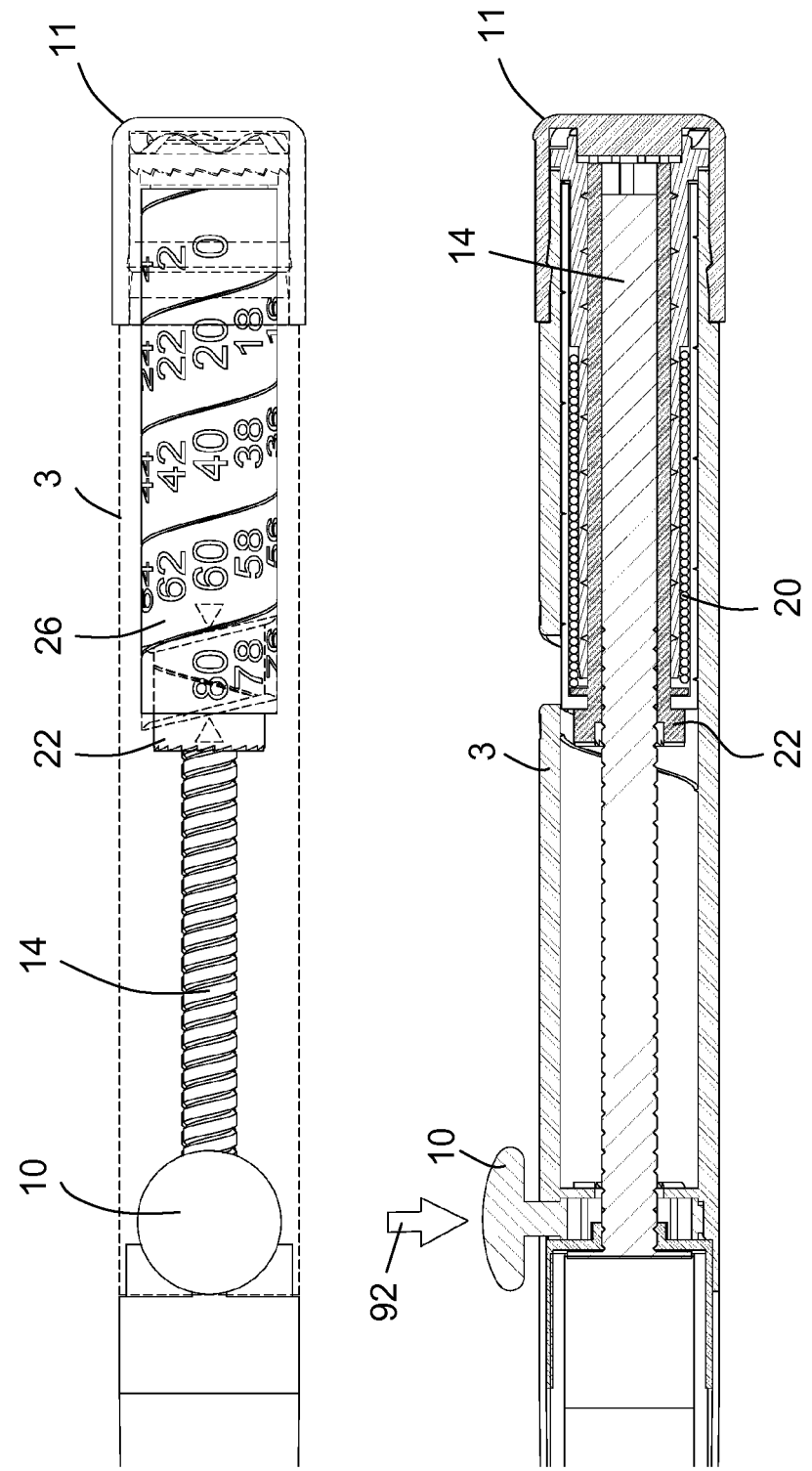
FIG. 17 shows the inner components and a cross-sectional view of the drive mechanism of the drug delivery device in a state where the maximum dose is dialled.

FIG. 17 shows a view and a cross-sectional view of the distal part of the drug delivery device in a state where the maximum dose is dialled.

In this state, the drive sleeve 22 engages with its maximum dose abutment on the thread 23 with the dial sleeve 24, so that the drive sleeve 22 reaches its most proximal position as well as the number sleeve 26. At this point, the maximum dose marking ("80") on the number sleeve 26 is visible in the window 23 of the body 3 indicating to the user that the maximum dose is set. The main spring 20 is fully charged and is held in its state by the ratchet means 51, 53 between the dial sleeve 24 and the body 3 as well as by the trigger member 9 engaging the trigger nut 18, which prevents rotational movement of the lead screw 14 and the drive sleeve 22, which is splined to the lead screw 14, with respect to the dial sleeve 24, thereby preventing unwinding of the main spring 20. In other words, the torque applied by the main spring 20 is reacted at the proximal end of the drive mechanism 4 via the ratchet means 51, 53 between the dial sleeve 24 and the body 3 and, at the distal end of the drive mechanism 4, by the trigger member 9 via the drive sleeve 22 and the trigger nut 18.

Cancelling a dose can be accomplished by rotating the dial member 11 in counter-clockwise direction 13. The user-applied torque, in combination with the main spring torque, is sufficient to overhaul the ratchet teeth between the dial sleeve 24 and the body 3. This returns the drive sleeve 22 and the number sleeve 26 towards the end-of-dose stop and progressively releases the torsion and compression of the main spring.

After setting the desired dose, drug delivery is initiated by pushing the trigger button 10 as indicated by arrow 92 in FIG. 17.

Figure 18:
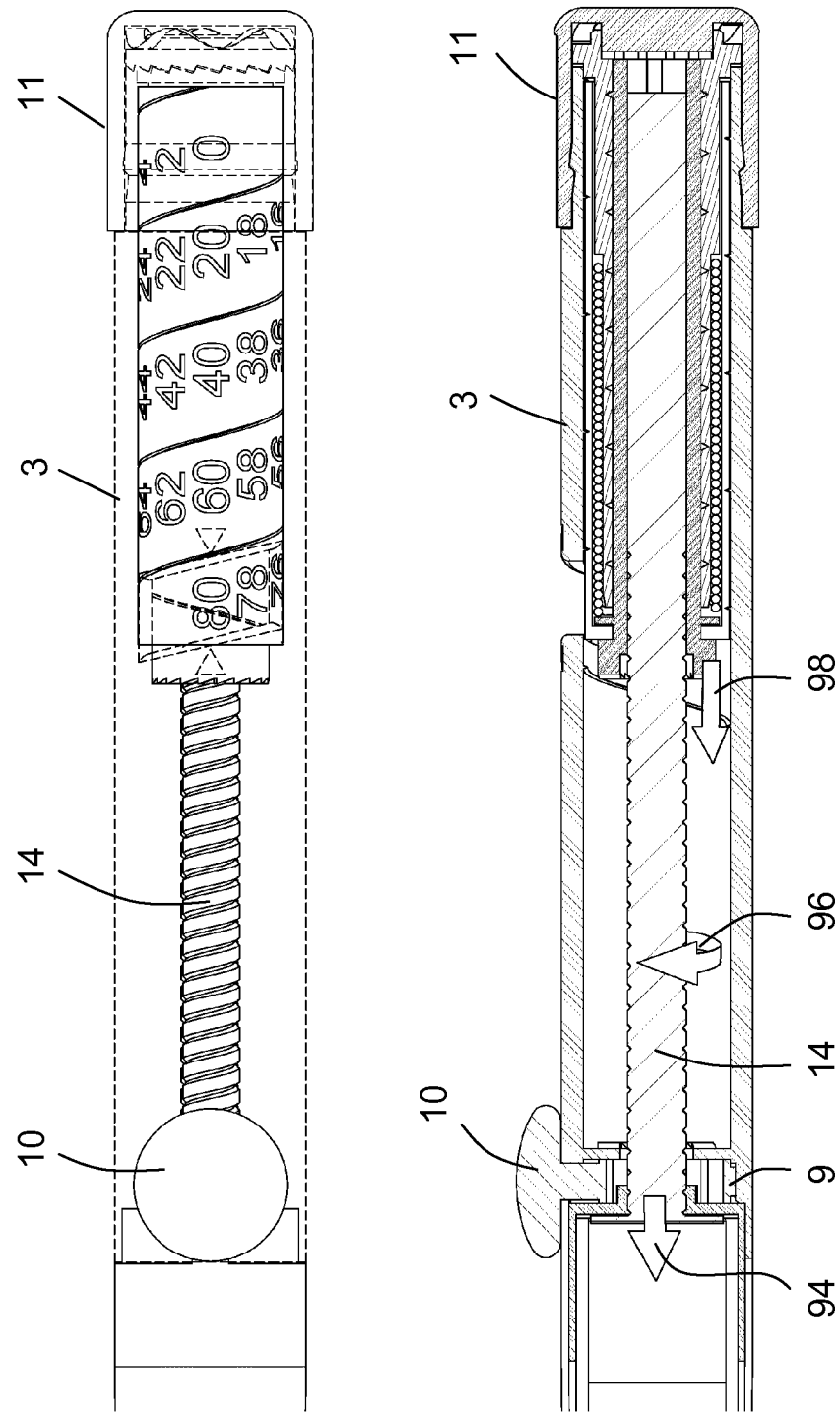
FIG. 18 shows the inner components and a cross-sectional view of the drive mechanism of the drug delivery device in a state where the trigger button is pushed.

FIG. 18 shows a view and a cross-sectional view of the distal part of the drug delivery device in a state where the trigger button 10 is pushed and the trigger member 9 is compressed.

The drug delivery device is triggered by the user by applying a force to the trigger button 10 in a direction perpendicular to the lead screw axis. Movement of the trigger button 10 towards the trigger member 9 releases the rotation of the trigger nut 18 with respect to the housing. As the trigger member 9 is deformed, the splines 54 engaged with the trigger nut 18 are released, allowing the trigger nut 18, the lead screw 14 and the drive sleeve 22 to rotate under the torque applied by the main spring 20, as indicated by arrow 96. The rotating lead screw 14 moves distally with respect to the thread insert 16, as indicated by arrow 94. Since the ratchet means 51, 53 fix the dial sleeve 24 to the body 3 and thereby one end of the main spring 20 connected with the dial sleeve 24 in its position, the rotational movement of the drive sleeve 22 with respect to dial sleeve 24 goes along with axial movement of the drive sleeve 22 and the number sleeve 26, as indicated by arrow 98. In other words, the lead screw 14 and the drive sleeve 22 move helically with respect to the housing during drug delivery.

The dial member 11 and the dial sleeve 24 do not rotate during dispense, retained by the ratchet means 51, 53 to the body 3. The drive sleeve 22 translates axially towards the end-of-dose stop as it rotates clockwise 12 during dispense. The number sleeve 26 translates axially with the drive sleeve 22, rotating due to the thread with the body 3 and displaying a reducing dose number through the window 23 in the body 3.

As the lead screw 14 is rotated by the drive sleeve 22, it translates in the distal direction via the thread 34 to the thread insert 16. The lead screw 14 drives the bung 7, which displaces the drug and dispenses the dose.

Figure 19:
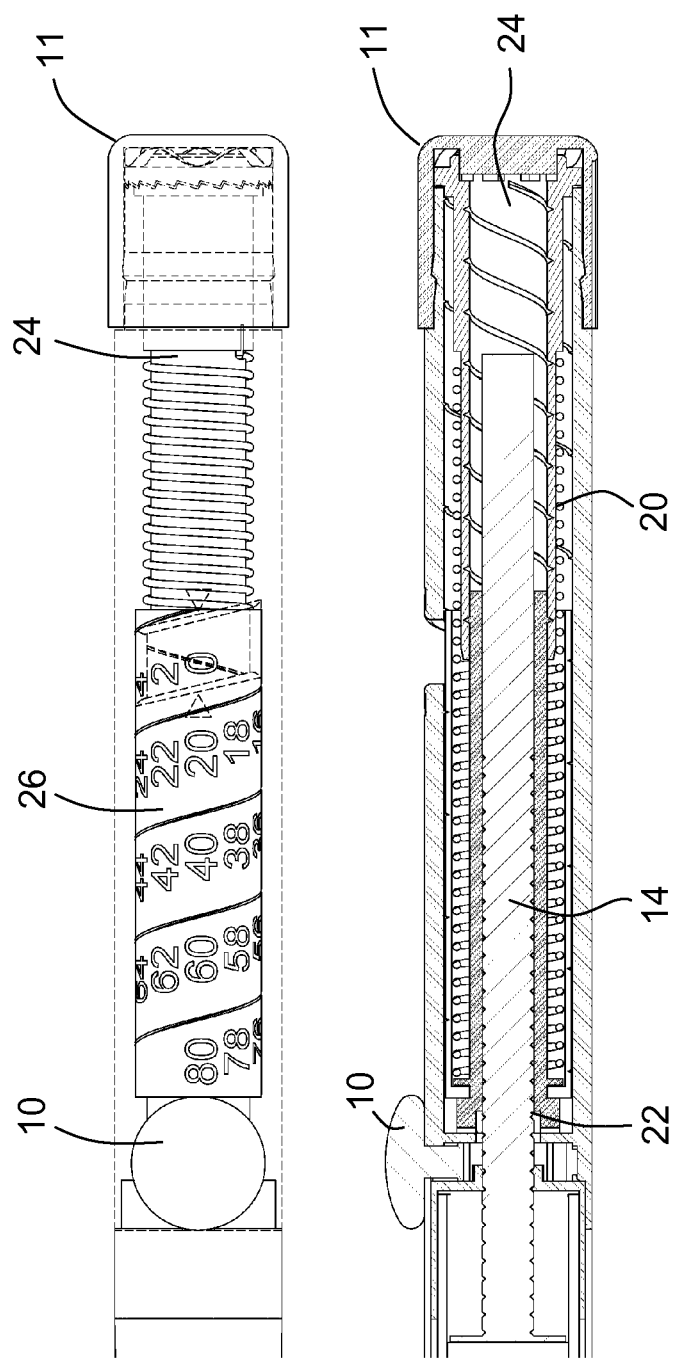
FIG. 19 shows the inner components and a cross-sectional view of the drive mechanism of the drug delivery device in a state at the end of delivery.

FIG. 19 shows a view and a cross-sectional view of the distal part of the drug delivery device in a state at the end of delivery.

Rotation of the trigger nut 18, the lead screw 11 and the drive sleeve 22 continues until the drive sleeve 22 gets in contact with the end-of-dose stop or the user releases the trigger button 10. The dose is completed when the end-ofdose stop is reached. In this case, the end-of-dose stop means of the housing and the drive sleeve 22 are in engagement. The drive sleeve 22, the number sleeve 26 and the main spring 20 have returned to their "at rest" states. The number display returns to "0".

Following completion of dose dispense, the user releases the trigger button 20, which re-engages the splines to the trigger nut 18 and returns the drug delivery device to the "at rest" state ready for dialling the subsequent dose. When the trigger member 9 is uncompressed, the drug delivery device is ready for dialling the next dose.

The disposable drug delivery device mechanism for the injection of user-selectable doses of liquid drug requires a low input force from the user during injection. The conceptual mechanism as described provides a platform for the development of a range of pen injector drug delivery devices that provide delivery of a user-variable drug dose with relatively low user input injection force. There is a potential for the variable dose to have any pre-defined maximum dose with a resolution to the nearest 0.01 ml or larger.

The design of a drive mechanism 4 as described above may be used in a medical drug delivery device that can be operated to deliver a number of user-variable doses of medicament from a cartridge 6 via a needle. The drug delivery device is disposable and is delivered to the user in a fully assembled condition ready for use.

The drive mechanism 4 uses a torsion spring 20 to store energy, which is charged as the user selects the dose required. This spring energy is stored until the drug delivery device is triggered for dispense, at which point the stored energy is used to deliver the medicament from the cartridge 6 to the user.

Any dose size between zero and a pre-defined maximum can be selected in increments to suit the drug and user profile. The drive mechanism 4 permits cancelling of a dose without any drug being dispensed by rotation of the dose selecting dial member 11 in the opposing direction to when selecting a dose.

Upon activation, the trigger 8 causes the drug delivery device to dispense the drug if the dose selected is greater than zero.

The features of the embodiments mentioned above may be combined.

REFERENCE NUMERALS 1 distal direction
2 proximal direction
3 body
4 drive mechanism
5 cartridge holder
6 cartridge
7 bung
8 trigger
9 trigger member
10 trigger button
11 dial member
12 clockwise direction
13 counter-clockwise direction
14 lead screw
15 bearing
16 thread insert
18 trigger nut
20 main spring
22 drive sleeve
23 thread
24 dial sleeve
25 thread
26 number sleeve
28 window
30 thread
31 shaft
32 spline
34 thread
36 protrusion
38 teeth
40 step
42 step
44 spring disc
46 flange
48 splines
50 up ramp
51 ratchet means
52 down ramp
53 ratchet means
54 protrusions
56 arrow
58 boss
60 boss
65 socket
64 spring end
66 spring end
68 flange
70 groove
72 thread
74 thread
76 thread
78 numbers
80 marker
84 teeth
85 ratchet means
86 teeth
90 arrow
92 arrow
94 arrow
96 arrow

The invention claimed is:

1. A drive mechanism for a drug delivery device, the drive mechanism comprising:
a piston rod,
a trigger nut that is axially movable with respect to the piston rod,
a trigger member surrounding the piston rod, the trigger member being coupled to the piston rod in such a manner that rotational movement between the piston rod and the trigger member is constrained in a first state, the trigger member being elastically deformable in such a manner that the piston rod is rotationally moveable with respect to the trigger member in a second state, and
a trigger button configured to deform the trigger member, wherein a movement of the trigger button towards the trigger nut causes elastic deformation of the trigger member, and wherein the trigger nut is located in a hole of the trigger member.

2. The drive mechanism according to claim 1, wherein the trigger nut is coupled to the piston rod in such a manner that rotational movement between the trigger nut and the piston rod is constrained,
wherein the trigger member engages with the trigger nut in such a manner that rotational movement between the trigger nut and the trigger member is constrained in the first state, the trigger member being elastically deformable in such a manner that the trigger member disengages from the trigger nut in the second state, thereby enabling rotational movement of the trigger nut with respect to the trigger member.

3. The drive mechanism according to claim 2, wherein the trigger member comprises a trigger engagement member engaging with a nut engagement means of the trigger nut, the trigger engagement member movable away from the nut engagement means, thereby disengaging from the nut engagement means, when the trigger member is deformed.

4. The drive mechanism according to claim 3, wherein the trigger engagement member is located offset to a connection between the trigger button and the trigger member.

5. The drive mechanism according to claim 3, wherein the trigger nut comprises a multitude of teeth that are located circumferentially, the trigger engagement member comprising a protrusion that is suitable for engaging with a gap between two teeth of the multitude of teeth of the trigger nut.

6. The drive mechanism according to claim 2, wherein the trigger nut is splined with the piston rod.

7. The drive mechanism according to claim 1, wherein the trigger button and the trigger member are made in one piece.

8. The drive mechanism according to claim 1, wherein the trigger member comprises a sleeve.

9. The drive mechanism according to claim 1, wherein the trigger member comprises at least one fixing member configured to be connected with a housing of the drug delivery device in order to fix a position of the trigger member with respect to the housing.

10. The drive mechanism according to claim 1, further comprising
a drive sleeve axially movable with respect to the piston rod, the drive sleeve being coupled to the piston rod in such a manner that rotational movement between the drive sleeve and the piston rod is constrained, and
a spring member coupled to the drive sleeve in such a manner that the spring member is compressed when the drive sleeve moves proximally with respect to the piston rod.

11. The drive mechanism according to claim 10, further comprising a dial sleeve being threadedly coupled to the drive sleeve, the spring member being connected with the dial sleeve in such a manner that the spring member is wound and/or compressed in the first state by a helical movement of the dial sleeve with respect to the drive sleeve, the spring member being configured to at least partly relax when rotational movement of the piston rod is allowed in the second state and to thereby rotate the drive sleeve with respect to the dial sleeve.

12. The drive mechanism according to claim 1, wherein the piston rod is a lead screw.

13. The drive mechanism according to claim 1, wherein the trigger member is sleeve-shaped.

14. The drive mechanism according to claim 1, wherein the trigger member comprises a sleeve-shaped portion defining the hole.

15. The drive mechanism according to claim 14, further comprising a fixing member protruding radially outwardly from the sleeve-shaped portion, the fixing member connecting the trigger member to the trigger button.

16. The drive mechanism according to claim 15, wherein the sleeve-shaped portion of the trigger member comprises an inner surface and an outer surface, the inner surface of the sleeve-shaped portion defining the hole, wherein the fixing member protrudes radially outwardly from the outer surface of the sleeve-shaped portion,
wherein the inner surface of the sleeve-shaped portion of the trigger member comprises a longitudinally extending protrusion engaged with the trigger nut to rotationally constrain the trigger nut.

17. A drug delivery device comprising:
a housing; and
a drive mechanism at least partially disposed within the housing, the drive mechanism comprising
a piston rod,
a trigger nut that is axially movable with respect to the piston rod,
a trigger member surrounding the piston rod, the trigger member being coupled to the piston rod in such a manner that rotational movement between the piston rod and the trigger member is constrained in a first state, the trigger member being elastically deformable in such a manner that the piston rod is rotationally moveable with respect to the trigger member in a second state, and
a trigger button being suitable configured to deform the trigger member, wherein a movement of the trigger button towards the trigger nut causes elastic deformation of the trigger member, and wherein the trigger nut is located in a hole of the trigger member.

18. A drug delivery device comprising:
a housing; and
a drive mechanism at least partially disposed within the housing, the drive mechanism comprising
a piston rod,
a trigger nut that is axially movable with respect to the piston rod,
a trigger member coupled to the piston rod in such a manner that rotational movement between the piston rod and the trigger member is constrained in a first state, the trigger member being elastically deformable in such a manner that the piston rod is rotationally moveable with respect to the trigger member in a second state, and
a trigger button configured to deform the trigger member, wherein a movement of the trigger button towards the trigger nut causes elastic deformation of the trigger member, and wherein the trigger member is centered along a longitudinal axis of the drug delivery device.

19. The drug delivery device according to claim 18, wherein the trigger member surrounds the piston rod.

* * * * *